(12) United States Patent  (10) Patent No.: US 11,160,583 B2
Lee et al.                 (45) Date of Patent:     Nov. 2, 2021

(54) OFFSET RODS, OFFSET ROD CONNECTORS, AND RELATED METHODS

(71) Applicant: Medos International Sàrl, Le Locle (CH)

(72) Inventors: Kevin Lee, Canton, MA (US); Ben Johnston, Quincy, MA (US); Frank Spratt, Middleboro, MA (US); Samuel Jacobs, Acton, MA (US)

(73) Assignee: Medos International Sarl, Le Locle (CH)

( * ) Notice: Subject to any disclaimer, the term of this patent is extended or adjusted under 35 U.S.C. 154(b) by 0 days.

(21) Appl. No.: 16/666,887

(22) Filed: Oct. 29, 2019

(65) Prior Publication Data
US 2020/0060729 A1    Feb. 27, 2020

Related U.S. Application Data

(63) Continuation of application No. 15/382,837, filed on Dec. 19, 2016, now Pat. No. 10,492,835.

(51) Int. Cl.
*A61B 17/70* (2006.01)

(52) U.S. Cl.
CPC ........ *A61B 17/705* (2013.01); *A61B 17/7011* (2013.01); *A61B 17/7032* (2013.01); *A61B 17/7082* (2013.01)

(58) Field of Classification Search
CPC .............. A61B 17/705; A61B 17/7011; A61B 17/7007; A61B 17/7008; A61B 17/7041; A61B 17/7004; A61B 17/7002; A61B 17/7032
USPC .......... 606/250, 260, 264, 265, 279
See application file for complete search history.

(56) References Cited

U.S. PATENT DOCUMENTS

| 5,261,909 A | 11/1993 | Sutterlin et al. |
| 5,312,405 A | 5/1994 | Korotko et al. |
| 5,569,246 A | 10/1996 | Ojima et al. |
| 5,613,968 A | 3/1997 | Lin |
| 5,667,506 A | 9/1997 | Sutterlin |
| 5,709,685 A | 1/1998 | Dombrowski et al. |
| 5,716,355 A | 2/1998 | Jackson et al. |

(Continued)

FOREIGN PATENT DOCUMENTS

| CN | 201194833 | * 2/2009 | ........ A61B 17/705 |
| EP | 1857064 A1 | 11/2007 | |

(Continued)

OTHER PUBLICATIONS

[No Author Listed] VuePoint II Technique Guide, 2015, NuVasive®, Inc.; 64 pages.

(Continued)

*Primary Examiner* — Eduardo C Robert
*Assistant Examiner* — David C Comstock
(74) *Attorney, Agent, or Firm* — Barnes & Thornburg LLP

(57) ABSTRACT

Devices and methods that allow a rod to be offset in a relatively small amount of space are disclosed herein. In some embodiments, first and second offset rods can be joined by a plate-type connector having a reduced thickness suitable for insertion into a small space, e.g., between adjacent bone anchors. In some embodiments, first and second offset rods can be joined by a curved connector that conforms to adjacent bone anchors and likewise has a reduced thickness.

23 Claims, 9 Drawing Sheets

(56) References Cited

U.S. PATENT DOCUMENTS

| | | |
|---|---|---|
| 5,725,528 A | 3/1998 | Errico et al. |
| 5,769,857 A | 6/1998 | Reztzov et al. |
| 5,776,135 A | 7/1998 | Errico et al. |
| 5,876,403 A | 3/1999 | Shitoto |
| 5,885,284 A | 3/1999 | Enico et al. |
| 5,980,523 A | 11/1999 | Jackson |
| 6,050,997 A | 4/2000 | Mullane |
| 6,083,226 A | 7/2000 | Fiz |
| 6,096,039 A | 8/2000 | Stoltenberg et al. |
| 6,231,575 B1 | 5/2001 | Krag |
| 6,238,396 B1 | 5/2001 | Lombardo |
| 6,248,104 B1 | 6/2001 | Chopin et al. |
| 6,280,443 B1 | 8/2001 | Gu et al. |
| 6,309,390 B1 | 10/2001 | Le Couedic et al. |
| 6,328,739 B1 | 12/2001 | Liu et al. |
| 6,328,740 B1 | 12/2001 | Richelsoph |
| 6,402,751 B1 | 6/2002 | Hoeck et al. |
| 6,468,276 B1 | 10/2002 | McKay |
| 6,478,798 B1 | 11/2002 | Howland |
| 6,524,310 B1 | 2/2003 | Lombardo et al. |
| 6,551,318 B1 | 4/2003 | Stahurski |
| 6,554,832 B2 | 4/2003 | Shluzas |
| 6,592,585 B2 | 7/2003 | Lee et al. |
| 6,616,668 B2 | 9/2003 | Altarec et al. |
| 6,676,661 B1 | 1/2004 | Benlloch et al. |
| 6,736,775 B2 | 5/2004 | Phillips |
| 6,736,820 B2 | 5/2004 | Biedermann et al. |
| 6,783,526 B1 | 8/2004 | Lin et al. |
| 6,786,907 B2 | 9/2004 | Lange |
| 6,793,657 B2 | 9/2004 | Lee et al. |
| 6,974,460 B2 | 12/2005 | Carbone et al. |
| 7,029,474 B2 | 4/2006 | Richelsoph et al. |
| 7,104,993 B2 | 9/2006 | Baynham et al. |
| 7,122,036 B2 | 10/2006 | Vanacker |
| 7,163,538 B2 | 1/2007 | Altarac et al. |
| 7,166,108 B2 | 1/2007 | Mazda et al. |
| 7,179,261 B2 | 2/2007 | Sicvol et al. |
| 7,189,236 B2 | 3/2007 | Taylor et al. |
| 7,485,132 B1 | 2/2009 | McBride et al. |
| 7,572,277 B2 | 8/2009 | Roussouly et al. |
| 7,575,587 B2 | 8/2009 | Rezach et al. |
| 7,585,314 B2 | 9/2009 | Taylor et al. |
| 7,628,799 B2 | 12/2009 | Richelsoph et al. |
| 7,666,210 B2 | 2/2010 | Franck et al. |
| 7,704,270 B2 | 4/2010 | De Coninck |
| 7,717,938 B2 | 5/2010 | Kim et al. |
| 7,717,940 B2 | 5/2010 | Woods et al. |
| 7,744,632 B2 | 6/2010 | Usher |
| 7,744,634 B2 | 6/2010 | Farris |
| 7,753,940 B2 | 7/2010 | Veldman et al. |
| 7,771,474 B2 | 8/2010 | Cordaro |
| 7,789,897 B2 | 9/2010 | Sanders |
| 7,794,478 B2 | 9/2010 | Nilsson |
| 7,803,174 B2 | 9/2010 | Denis et al. |
| 7,806,912 B2 | 10/2010 | Lawton et al. |
| 7,833,248 B2 | 11/2010 | Markworth et al. |
| 7,837,714 B2 | 11/2010 | Drewry et al. |
| 7,842,071 B2 | 11/2010 | Hawkes |
| 7,901,434 B2 | 3/2011 | Drewry et al. |
| 7,909,854 B2 | 3/2011 | Schwab |
| 7,922,746 B2 | 4/2011 | Miller |
| 7,922,747 B2 | 4/2011 | Kirschman |
| 7,927,355 B2 | 4/2011 | Berrevoets et al. |
| 7,942,901 B2 | 5/2011 | Rezach |
| 7,947,066 B2 | 5/2011 | Tepper et al. |
| 7,959,653 B2 | 6/2011 | Thramann et al. |
| 7,993,371 B2 | 8/2011 | Farris |
| 8,016,862 B2 | 9/2011 | Felix et al. |
| 8,025,679 B2 | 9/2011 | Nichols et al. |
| 8,062,338 B2 | 11/2011 | McBride et al. |
| 8,075,594 B2 | 12/2011 | Purcell |
| 8,080,037 B2 | 12/2011 | Butler et al. |
| 8,097,022 B2 | 1/2012 | Marik |
| 8,109,974 B2 | 2/2012 | Boomer et al. |
| 8,114,133 B2 | 2/2012 | Logan |
| 8,147,519 B2 | 4/2012 | Wilcox |
| 8,152,851 B2 | 4/2012 | Mueller et al. |
| 8,167,908 B2 | 5/2012 | Ely et al. |
| 8,172,879 B2 | 5/2012 | Butler et al. |
| 8,192,467 B2 | 6/2012 | Felix et al. |
| 8,197,515 B2 | 6/2012 | Levy et al. |
| 8,236,028 B2 | 8/2012 | Kalfas et al. |
| 8,241,334 B2 | 8/2012 | Butler et al. |
| 8,246,657 B1 | 8/2012 | Samuel |
| 8,246,665 B2 | 8/2012 | Butler et al. |
| 8,262,700 B2 | 9/2012 | Cho et al. |
| 8,262,701 B2 | 9/2012 | Rathbun et al. |
| 8,292,924 B2 | 10/2012 | Neary et al. |
| 8,298,266 B2 | 10/2012 | Miller |
| 8,298,269 B2 | 10/2012 | Null et al. |
| 8,317,837 B2 | 11/2012 | Rezach et al. |
| 8,337,527 B2 | 12/2012 | Hawkins et al. |
| 8,337,532 B1 | 12/2012 | McLean et al. |
| 8,366,749 B2 | 2/2013 | Sweeney |
| 8,366,750 B2 | 2/2013 | Iott et al. |
| 8,414,616 B2 | 4/2013 | Berrevoets et al. |
| 8,414,617 B2 | 4/2013 | Young et al. |
| 8,419,771 B2 | 4/2013 | Poirier et al. |
| 8,419,773 B2 | 4/2013 | Biedermann et al. |
| 8,430,916 B2 | 4/2013 | Winslow et al. |
| 8,460,342 B2 | 6/2013 | Courtney et al. |
| 8,470,001 B2 | 6/2013 | Trautwein et al. |
| 8,591,550 B2 | 11/2013 | Ludwig et al. |
| 8,617,213 B2 | 12/2013 | Moore et al. |
| 8,628,559 B2 | 1/2014 | Iott et al. |
| 8,641,739 B2 | 2/2014 | McLean et al. |
| 8,657,856 B2 | 2/2014 | Gephart et al. |
| 8,668,721 B2 | 3/2014 | Miller |
| 8,715,323 B2 | 5/2014 | Ballard et al. |
| 8,721,689 B2 | 5/2014 | Butler et al. |
| 8,728,124 B2 | 5/2014 | Miller |
| 8,758,411 B1 | 6/2014 | Rayon et al. |
| 8,771,319 B2 | 7/2014 | Prajapati |
| 8,808,332 B2 | 8/2014 | Iott et al. |
| 8,828,056 B2 | 9/2014 | Buss et al. |
| 8,864,798 B2 | 10/2014 | Weiman et al. |
| 8,864,799 B2 | 10/2014 | Kraus |
| 8,870,923 B2 | 10/2014 | Richelsoph |
| 8,882,803 B2 | 11/2014 | Iott et al. |
| 8,888,777 B2 | 11/2014 | Mullaney |
| 8,888,819 B2 | 11/2014 | Frasier et al. |
| 8,920,471 B2 | 12/2014 | Barrus et al. |
| 8,920,475 B1 | 12/2014 | Ziemek et al. |
| 8,945,186 B2 | 2/2015 | Walker et al. |
| 8,951,289 B2 | 2/2015 | Matityahu |
| 8,998,956 B2 | 4/2015 | George et al. |
| 8,998,961 B1 | 4/2015 | Ziemek et al. |
| 9,005,249 B2 | 4/2015 | Rinner et al. |
| 9,023,087 B2 | 5/2015 | Frankel et al. |
| 9,055,980 B2 | 6/2015 | Biedermann |
| 9,060,815 B1 | 6/2015 | Gustine et al. |
| 9,072,547 B2 | 7/2015 | Harper et al. |
| 9,084,630 B2 | 7/2015 | Mullaney |
| 9,095,380 B2 | 8/2015 | Mir et al. |
| 9,101,400 B2 | 8/2015 | Trieu et al. |
| 9,101,405 B2 | 8/2015 | Dickinson et al. |
| 9,107,703 B2 | 8/2015 | Torres |
| 9,113,961 B2 | 8/2015 | Larroque-Lahitette |
| 9,119,675 B2 | 9/2015 | Lee et al. |
| 9,125,691 B2 | 9/2015 | Gunn |
| 9,131,963 B2 | 9/2015 | Predick |
| 9,131,964 B2 | 9/2015 | Blain et al. |
| 9,149,301 B2 | 10/2015 | Asaad et al. |
| 9,155,565 B2 | 10/2015 | Boomer et al. |
| 9,155,580 B2 | 10/2015 | Cormier et al. |
| 9,186,184 B2 | 11/2015 | Janowski |
| 9,198,696 B2 | 12/2015 | Bannigan et al. |
| 9,204,901 B2 | 12/2015 | Black et al. |
| 9,220,541 B1 | 12/2015 | Dant et al. |
| 9,247,964 B1 | 2/2016 | Shoshtaev |
| 9,265,548 B2 | 2/2016 | Jones et al. |
| 9,271,763 B2 | 3/2016 | Barrus et al. |
| 9,339,307 B2 | 5/2016 | McClintock et al. |
| 9,345,521 B2 | 5/2016 | Ziolo |

(56) References Cited

U.S. PATENT DOCUMENTS

| | | |
|---|---|---|
| 9,421,041 B2 | 8/2016 | Richelsoph |
| 9,433,445 B2 | 9/2016 | Ramsay et al. |
| 9,451,994 B1 | 9/2016 | Whipple et al. |
| 9,474,554 B2 | 10/2016 | Strnad |
| 9,517,089 B1 | 12/2016 | Casey et al. |
| 9,561,058 B2 | 2/2017 | Lange et al. |
| 9,579,126 B2 | 2/2017 | Zhang et al. |
| 9,615,867 B2 | 4/2017 | Picetti et al. |
| 9,629,663 B2 | 4/2017 | Ludwig et al. |
| 9,649,136 B2 | 5/2017 | George et al. |
| 9,693,808 B2 | 7/2017 | Fauth et al. |
| 9,724,131 B2 | 8/2017 | Bootwala et al. |
| 9,770,269 B1 | 9/2017 | Shoshtaev |
| 9,956,009 B1 | 5/2018 | Shoshtaev |
| 10,238,432 B2 | 3/2019 | Carruth et al. |
| 10,321,939 B2 | 6/2019 | Lee et al. |
| 10,398,476 B2 | 9/2019 | Lee et al. |
| 10,492,835 B2 | 12/2019 | Lee et al. |
| 10,517,647 B2 | 12/2019 | Lee et al. |
| 10,561,454 B2 | 2/2020 | Lee et al. |
| 10,869,695 B2 | 12/2020 | Carruth et al. |
| 2002/0042614 A1 | 4/2002 | Ueyama et al. |
| 2003/0045878 A1 | 3/2003 | Petit et al. |
| 2003/0045879 A1 | 3/2003 | Minfelde et al. |
| 2003/0153914 A1 | 8/2003 | Oribe et al. |
| 2004/0111088 A1 | 6/2004 | Picetti et al. |
| 2004/0147929 A1 | 7/2004 | Biedermann et al. |
| 2004/0162558 A1 | 8/2004 | Hegde et al. |
| 2005/0131404 A1 | 6/2005 | Mazda et al. |
| 2005/0171537 A1 | 8/2005 | Mazel et al. |
| 2005/0228326 A1 | 10/2005 | Kalfas et al. |
| 2005/0228377 A1 | 10/2005 | Chao et al. |
| 2005/0228378 A1 | 10/2005 | Kalfas et al. |
| 2005/0228382 A1 | 10/2005 | Richelsoph et al. |
| 2006/0039750 A1 | 2/2006 | Thomke et al. |
| 2006/0058789 A1 | 3/2006 | Kim et al. |
| 2006/0064090 A1* | 3/2006 | Park ................ A61B 17/7026 606/250 |
| 2006/0064091 A1 | 3/2006 | Ludwig et al. |
| 2006/0079892 A1 | 4/2006 | Roychowdhury et al. |
| 2006/0177263 A1 | 8/2006 | Thomke et al. |
| 2006/0206114 A1 | 9/2006 | Ensign et al. |
| 2006/0229611 A1 | 10/2006 | Avery et al. |
| 2006/0241598 A1 | 10/2006 | Khalili |
| 2006/0282074 A1 | 12/2006 | Renaud et al. |
| 2007/0049932 A1 | 3/2007 | Richelsoph et al. |
| 2007/0100339 A1 | 5/2007 | Clement et al. |
| 2007/0123860 A1 | 5/2007 | Francis et al. |
| 2007/0173825 A1 | 7/2007 | Sharifi-Mehr et al. |
| 2007/0173829 A1 | 7/2007 | Drewry et al. |
| 2007/0233062 A1 | 10/2007 | Berry |
| 2007/0233090 A1 | 10/2007 | Naifeh et al. |
| 2007/0250061 A1 | 10/2007 | Chin et al. |
| 2007/0270805 A1 | 11/2007 | Miller et al. |
| 2007/0270817 A1 | 11/2007 | Rezach |
| 2007/0270818 A1 | 11/2007 | Rezach |
| 2007/0276384 A1 | 11/2007 | Spratt |
| 2008/0021466 A1* | 1/2008 | Shadduck .......... A61B 17/7062 606/249 |
| 2008/0045963 A1 | 2/2008 | Abdou |
| 2008/0058805 A1 | 3/2008 | Stuart |
| 2008/0082112 A1 | 4/2008 | Lawton et al. |
| 2008/0109039 A1 | 5/2008 | Michielli et al. |
| 2008/0177318 A1 | 7/2008 | Veldman et al. |
| 2008/0177323 A1 | 7/2008 | Null et al. |
| 2008/0234743 A1 | 9/2008 | Marik |
| 2008/0255617 A1 | 10/2008 | Cho et al. |
| 2008/0262552 A1 | 10/2008 | Kim |
| 2008/0262553 A1 | 10/2008 | Hawkins et al. |
| 2008/0269810 A1 | 10/2008 | Zhang et al. |
| 2008/0281361 A1 | 11/2008 | Vittur et al. |
| 2009/0036929 A1 | 2/2009 | Reglos et al. |
| 2009/0082812 A1 | 3/2009 | Lewis |
| 2009/0105765 A1 | 4/2009 | Strnad |
| 2009/0157120 A1 | 6/2009 | Marino et al. |
| 2009/0163956 A1 | 6/2009 | Biedermann et al. |
| 2009/0187217 A1 | 7/2009 | Weiman et al. |
| 2009/0204153 A1 | 8/2009 | Suzuki et al. |
| 2009/0222042 A1 | 9/2009 | Firkins et al. |
| 2009/0228046 A1 | 9/2009 | Garamszegi |
| 2009/0249851 A1* | 10/2009 | Isaacs .................... G06F 30/00 72/31.04 |
| 2010/0004686 A1* | 1/2010 | Lemoine ............ A61B 17/705 606/246 |
| 2010/0004693 A1 | 1/2010 | Miller et al. |
| 2010/0010545 A1 | 1/2010 | Park et al. |
| 2010/0087864 A1 | 4/2010 | Klein et al. |
| 2010/0087867 A1 | 4/2010 | Klein et al. |
| 2010/0094345 A1 | 4/2010 | Saidha et al. |
| 2010/0094346 A1 | 4/2010 | Matityahu |
| 2010/0094349 A1 | 4/2010 | Hammer et al. |
| 2010/0114165 A1* | 5/2010 | Ely .................... A61B 17/8605 606/246 |
| 2010/0114167 A1 | 5/2010 | Wilcox et al. |
| 2010/0160981 A1 | 6/2010 | Butler et al. |
| 2010/0204733 A1 | 8/2010 | Rathbun et al. |
| 2010/0241171 A1 | 9/2010 | Clement et al. |
| 2010/0274286 A1 | 10/2010 | Blain et al. |
| 2010/0280552 A1 | 11/2010 | Lee |
| 2010/0298884 A1 | 11/2010 | Faizan et al. |
| 2010/0324599 A1 | 12/2010 | Montello et al. |
| 2011/0034957 A1 | 2/2011 | Biedermann |
| 2011/0046675 A1 | 2/2011 | Barrus et al. |
| 2011/0066187 A1 | 3/2011 | Fang et al. |
| 2011/0087287 A1 | 4/2011 | Reeder, Jr. et al. |
| 2011/0087288 A1 | 4/2011 | Stevenson et al. |
| 2011/0098748 A1 | 4/2011 | Jangra |
| 2011/0106178 A1 | 5/2011 | Schwab |
| 2011/0112533 A1 | 5/2011 | Venturini et al. |
| 2011/0112580 A1 | 5/2011 | Clement et al. |
| 2011/0137345 A1 | 6/2011 | Stoll et al. |
| 2011/0152936 A1 | 6/2011 | Gil et al. |
| 2011/0196425 A1 | 8/2011 | Rezach et al. |
| 2011/0245872 A1 | 10/2011 | Nilsson |
| 2011/0245878 A1 | 10/2011 | Franks et al. |
| 2011/0307018 A1 | 12/2011 | Zucherman et al. |
| 2012/0029571 A1 | 2/2012 | Schwab et al. |
| 2012/0059421 A1 | 3/2012 | Aferzon |
| 2012/0071926 A1 | 3/2012 | Jani et al. |
| 2012/0083845 A1 | 4/2012 | Winslow et al. |
| 2012/0095512 A1 | 4/2012 | Nihalani |
| 2012/0130436 A1 | 5/2012 | Haskins et al. |
| 2012/0158064 A1 | 6/2012 | Kroll |
| 2012/0203278 A1 | 8/2012 | Gil et al. |
| 2012/0221053 A1 | 8/2012 | Copf |
| 2012/0226316 A1 | 9/2012 | Dant et al. |
| 2012/0232593 A1 | 9/2012 | Predick |
| 2012/0259369 A1 | 10/2012 | Hammer |
| 2012/0290013 A1 | 11/2012 | Simonson |
| 2012/0296335 A1 | 11/2012 | Mullaney |
| 2012/0303062 A1 | 11/2012 | Amstutz et al. |
| 2013/0018422 A1 | 1/2013 | Rinner et al. |
| 2013/0030468 A1 | 1/2013 | Le Couedic et al. |
| 2013/0079826 A1 | 3/2013 | Simonson |
| 2013/0085534 A1 | 4/2013 | Hainard et al. |
| 2013/0096617 A1 | 4/2013 | Ballard et al. |
| 2013/0123854 A1 | 5/2013 | Kondrashov et al. |
| 2013/0211457 A1 | 8/2013 | Dickinson et al. |
| 2013/0253588 A1 | 9/2013 | Traynelis et al. |
| 2013/0268004 A1 | 10/2013 | Rathbun |
| 2013/0274807 A1 | 10/2013 | Prajapati |
| 2013/0274808 A1 | 10/2013 | Larroque-Lahitette et al. |
| 2014/0018858 A1 | 1/2014 | Laeng et al. |
| 2014/0066990 A1 | 3/2014 | Akbarnia et al. |
| 2014/0088650 A1 | 3/2014 | Taddia et al. |
| 2014/0114359 A1 | 4/2014 | Hawkes |
| 2014/0135839 A1 | 5/2014 | Frankel et al. |
| 2014/0148856 A1 | 5/2014 | Ibarra et al. |
| 2014/0222076 A1* | 8/2014 | Jackson ............. A61B 17/7049 606/265 |
| 2014/0249581 A1 | 9/2014 | Stachniak |
| 2014/0277146 A1 | 9/2014 | Li et al. |
| 2014/0277160 A1 | 9/2014 | Ziolo |
| 2014/0277163 A1 | 9/2014 | Kretzer et al. |

(56) References Cited

U.S. PATENT DOCUMENTS

| | | |
|---|---|---|
| 2014/0303674 A1 | 10/2014 | Sasing |
| 2014/0316468 A1 | 10/2014 | Keiser et al. |
| 2014/0336706 A1 | 11/2014 | Garamszegi |
| 2014/0343613 A1 | 11/2014 | Eliasen et al. |
| 2015/0032160 A1 | 1/2015 | Carbone et al. |
| 2015/0057707 A1 | 2/2015 | Barrus et al. |
| 2015/0057708 A1 | 2/2015 | Ballard et al. |
| 2015/0073479 A1 | 3/2015 | Rinner |
| 2015/0094769 A1 | 4/2015 | Abbasi |
| 2015/0119941 A1 | 4/2015 | Daniels et al. |
| 2015/0190178 A1 | 7/2015 | McCarthy et al. |
| 2015/0196328 A1 | 7/2015 | Hirschl et al. |
| 2015/0223844 A1 | 8/2015 | Leff et al. |
| 2015/0230830 A1 | 8/2015 | Frankel et al. |
| 2015/0282842 A1* | 10/2015 | Beyar ............... A61B 17/7037 606/273 |
| 2015/0313645 A1 | 11/2015 | Hansell |
| 2015/0359568 A1 | 12/2015 | Rezach |
| 2016/0135846 A1 | 5/2016 | Mirda |
| 2016/0143665 A1 | 5/2016 | Biedermann et al. |
| 2016/0166289 A1 | 6/2016 | Alsup et al. |
| 2016/0287294 A1 | 10/2016 | Kubo et al. |
| 2017/0020578 A1 | 1/2017 | Mosnier et al. |
| 2017/0079690 A1 | 3/2017 | Oberlander et al. |
| 2017/0086885 A1 | 3/2017 | Duncan et al. |
| 2017/0086895 A1 | 3/2017 | Barra et al. |
| 2017/0095271 A1 | 4/2017 | Faulhaber |
| 2017/0105764 A1* | 4/2017 | Williams ............. A61B 17/705 |
| 2017/0112540 A1 | 4/2017 | Montello et al. |
| 2017/0119439 A1 | 5/2017 | Ozdil et al. |
| 2017/0128105 A1 | 5/2017 | Patrinicola et al. |
| 2017/0128107 A1 | 5/2017 | Alsup et al. |
| 2017/0209182 A1 | 7/2017 | Picetti et al. |
| 2017/0245900 A1 | 8/2017 | Rezach |
| 2017/0281247 A1 | 10/2017 | Murray et al. |
| 2017/0311985 A1 | 11/2017 | Bobbitt et al. |
| 2017/0333087 A1 | 11/2017 | Lee et al. |
| 2017/0333088 A1 | 11/2017 | Lee et al. |
| 2017/0348026 A1 | 12/2017 | Stein et al. |
| 2018/0042647 A1 | 2/2018 | Cowan et al. |
| 2018/0098798 A1* | 4/2018 | Italiaie ............... A61B 17/7083 |
| 2018/0116695 A1 | 5/2018 | Armstrong et al. |
| 2018/0161073 A1 | 6/2018 | Lee et al. |
| 2018/0168694 A1 | 6/2018 | Lee et al. |
| 2018/0195150 A1 | 7/2018 | Meyer et al. |
| 2018/0206890 A1 | 7/2018 | Rezach |
| 2018/0228516 A1 | 8/2018 | Armstrong et al. |
| 2018/0228518 A1 | 8/2018 | Carruth et al. |
| 2018/0243009 A1 | 8/2018 | Bobbitt et al. |
| 2018/0280062 A1 | 10/2018 | Lee et al. |
| 2018/0280063 A1 | 10/2018 | Lee et al. |
| 2018/0317972 A1 | 11/2018 | Abbasi |
| 2019/0167313 A1 | 6/2019 | Ortiz et al. |
| 2019/0175226 A1 | 6/2019 | Carruth et al. |
| 2019/0183541 A1 | 6/2019 | Lee et al. |
| 2019/0269440 A1 | 9/2019 | Patrinicola et al. |
| 2019/0336178 A1 | 11/2019 | Finn et al. |
| 2019/0365432 A1 | 12/2019 | Lee et al. |
| 2020/0069341 A1 | 3/2020 | Abbasi |
| 2020/0085473 A1 | 3/2020 | Lee et al. |
| 2020/0170695 A1 | 6/2020 | Lee et al. |
| 2021/0068872 A1 | 3/2021 | Carruth et al. |

FOREIGN PATENT DOCUMENTS

| | | | | |
|---|---|---|---|---|
| EP | 2 319 436 A1 | | 5/2011 | |
| EP | 2730242 A1 | | 5/2014 | |
| KR | 20100054713 | * | 5/2010 | ........... A61B 17/705 |
| WO | 2005/044119 A2 | | 5/2005 | |
| WO | WO-2007124242 A1 | * | 11/2007 | ........... A61B 17/705 |
| WO | 2009/110865 A8 | | 12/2009 | |
| WO | 2011/004222 A1 | | 1/2011 | |
| WO | 2011/006155 A1 | | 1/2011 | |
| WO | 2015/017250 A1 | | 2/2015 | |

OTHER PUBLICATIONS

Akbamia, B., et al., "Pediatric Isola® Prebent Rod Placement," (Technique Manual), DePuy Acromed, Oct. 2010; 2 pages.

International Search Report and Written Opinion for Application No. PCT/US2017/031883, dated Aug. 2, 2017. (15 pgs).

Invitation to Pay Additional Fees for Application No. PCT/US2018/017034, dated May 18, 2018 (18 pages).

International Search Report and Written Opinion for Application No. PCT/US2018/024731, dated Jul. 2, 2018 (17 pages).

International Search Report and Written Opinion for Application No. PCT/US2018/062786, dated Feb. 4, 2019 (15 pages).

U.S. Appl. No. 15/158,127, filed May 18, 2016, Implant Connectors and Related Methods.

U.S. Appl. No. 15/377,449, filed Dec. 13, 2016, Implant Adaptors and Related Methods.

U.S. Appl. No. 15/382,837, filed Dec. 19, 2016, Offset Rods, Offset Rod Connectors, and Related Methods.

U.S. Appl. No. 15/284,587, filed Oct. 4, 2016, Implant Connectors and Related Methods.

U.S. Appl. No. 15/430,188, filed Feb. 10, 2017, Tandem Rod Connectors and Related Methods.

U.S. Appl. No. 15/471,075, filed Mar. 28, 2017, Articulating Implant Connectors and Related Methods.

U.S. Appl. No. 15/828,805, filed Dec. 1, 2017, Rod-To-Rod Connectors Having Robust Rod Closure Mechanisms and Related Methods.

U.S. Appl. No. 15/843,618, filed Dec. 15, 2017, Unilateral Implant Holders and Related Methods.

U.S. Appl. No. 15/926,051, filed Mar. 20, 2018, Articulating Implant Connectors and Related Methods.

U.S. Appl. No. 16/280,918, filed Feb. 20, 2019, Tandem Rod Connectors and Related Methods.

U.S. Appl. No. 16/443,849, filed Jun. 17, 2019, Implant Connectors and Related Methods.

U.S. Appl. No. 16/688,578, filed Nov. 19, 2019, Implant Connectors and Related Methods.

U.S. Appl. No. 16/782,030, filed Feb. 4, 2020, Articulating Implant Connectors and Related Methods.

International Search Report and Written Opinion for Application No. PCT/US2018/017034, dated Aug. 1, 2018 (20 pages).

* cited by examiner

OFFSET RODS, OFFSET ROD CONNECTORS, AND RELATED METHODS

CROSS-REFERENCE TO RELATED APPLICATIONS

This application is a continuation of U.S. application Ser. No. 15/382,837, filed on Dec. 19, 2016, which is hereby incorporated by reference in its entirety.

FIELD

Orthopedic devices and methods are disclosed herein, including offset rods, offset rod connectors, and related methods.

BACKGROUND

Fixation systems can be used in orthopedic surgery to align and/or fix a desired relationship between two or more bones or bone fragments. For example, in spinal surgery, spinal fixation systems can be used to align and/or fix a desired relationship between vertebrae. A typical spinal fixation system can include bone screws or other anchors implanted in the vertebrae and connected by longitudinal rods.

There are a number of instances in which it can be desirable or necessary for a rod to include a lateral offset along its length. For example, in a construct that includes pedicle screws and lateral mass screws, a rod offset may be required at the transition between a pedicle screw and an adjacent lateral mass screw. Existing approaches for offsetting the rod include using a rod that is bent or using a rod-to-rod connector to connect two separate rods arranged in tandem. These existing approaches require a relatively large amount of space to achieve the desired offset. As a result, the surgeon must often skip over a vertebral level when attaching the fixation system to leave enough room for the lateral transition of the rod.

Accordingly, a need exists for devices and methods that allow a rod to be offset in a relatively small amount of space.

SUMMARY

Devices and methods that allow a rod to be offset in a relatively small amount of space are disclosed herein. In some embodiments, first and second offset rods can be joined by a plate-type connector having a reduced thickness suitable for insertion into a small space, e.g., between adjacent bone anchors. In some embodiments, first and second offset rods can be joined by a curved connector that conforms to adjacent bone anchors and likewise has a reduced thickness.

In some embodiments, a spinal implant system includes a connector having a superior surface from which a first rod extends and an inferior surface from which a second rod extends, the first and second rods being laterally offset from each other; a first bone anchor having a first head configured to receive the first rod therein such that the first rod extends along a first rod axis of the first head, the first head having a thickness T1 along the first rod axis; and a second bone anchor having a second head configured to receive the second rod therein such that the second rod extends along a second rod axis of the second head, the second head having a thickness T2 along the second rod axis; wherein the connector has a thickness TC between the superior and inferior surfaces of the connector; and wherein the ratio of TC:T1 is less than 0.75.

The ratio of TC:T1 can be less than 0.50. The ratio of TC:T1 can be less than 0.33. The ratio of TC:T2 can be less than 0.75. The ratio of TC:T2 can be less than 0.50. The ratio of TC:T2 can be less than 0.33. The first and second rods can be formed integrally with the connector. The first and second rods can be welded, keyed, pinned, snap-fitted, or interference-fitted to the connector. The first and second rods can be threaded into respective recesses formed in the connector. The connector can include a central portion that extends between opposed lateral portions, the thickness TC can be defined at the central portion and the opposed lateral portions can include thicknesses between the superior and inferior surfaces that are greater than TC. The superior surface of the connector can include a first recess in which the first rod is received; the inferior surface of the connector can include a second recess in which the second rod is received; the superior surface of the connector can include a first drive interface opposite to and axially aligned with the second recess; and the inferior surface of the connector can include a second drive interface opposite to and axially aligned with the first recess. The superior surface of the connector can conform to a sidewall surface of the head of the first bone anchor and the inferior surface of the connector can conform to a sidewall surface of the head of the second bone anchor.

In some embodiments, a spinal implant system includes a connector having a superior surface from which a first rod extends and an inferior surface from which a second rod extends, the first and second rods being laterally offset from each other; wherein the first rod has a diameter D1; wherein the second rod has a diameter D2; wherein the connector has a thickness TC between the superior and inferior surfaces of the connector; and wherein the ratio of TC:D1 is less than 1.

The ratio of TC:D1 can be less than 0.75. The ratio of TC:D1 can be less than 0.50. The ratio of TC:D2 can be less than 1. The ratio of TC:D2 can be less than 0.75. The ratio of TC:D2 can be less than 0.50. The first and second rods can be formed integrally with the connector. The first and second rods can be welded, keyed, pinned, snap-fitted, or interference-fitted to the connector. The first and second rods can be threaded into respective recesses formed in the connector. The connector can include a central portion that extends between opposed lateral portions, the thickness TC can be defined at the central portion and the opposed lateral portions can have thicknesses between the superior and inferior surfaces that are greater than TC. The superior surface of the connector can include a first recess in which the first rod is received; the inferior surface of the connector can include a second recess in which the second rod is received; the superior surface of the connector can include a first drive interface opposite to and axially aligned with the second recess; and the inferior surface of the connector can include a second drive interface opposite to and axially aligned with the first recess.

In some embodiments, a spinal implant connector includes a superior surface, an inferior surface, a central portion, first and second lateral portions on opposite sides of the central portion, a first drive interface formed in the superior surface and in the first lateral portion, a first rod recess formed in the superior surface and in the second lateral portion, a second rod recess formed in the inferior surface and in the first lateral portion, and a second drive interface formed in the inferior surface and in the second lateral portion.

The first and second recesses can be threaded. The first and second rod recesses can be welded, keyed, pinned, snap-fitted, or interference-fitted to first and second rods disposed therein. The connector can be S-shaped. The connector can provide a relief for an adjacent bone anchor. The central portion can have a thickness between the superior and inferior surfaces that is less than a thickness of the first lateral portion between the superior and inferior surfaces and less than a thickness of the second lateral portion between the superior and inferior surfaces. The first and second drive interfaces can be formed in respective convex portions of the superior and inferior surfaces. The superior surface can include a convex portion in which the first drive interface is formed, a planar portion in which the first rod recess is formed, and a curved portion connecting the convex portion and the planar portion. The inferior surface can include a convex portion in which the second drive interface is formed, a planar portion in which the second rod recess is formed, and a curved portion connecting the convex portion and the planar portion.

In some embodiments, a surgical method includes implanting a first bone anchor in a first vertebra of a spine of a patient; implanting a second bone anchor in a second vertebra of the spine; and positioning a connector such that: a first rod extending from the connector is seated in the first bone anchor; a second rod extending from the connector is seated in the second bone anchor; a superior surface of the connector contacts an inferior surface of the first bone anchor; and an inferior surface of the connector contacts a superior surface of the second bone anchor.

The superior surface of the connector can conform to the first bone anchor and the inferior surface of the connector can conform to the second bone anchor. The superior surface of the connector can provide a relief to the first bone anchor and the inferior surface of the connector can provide a relief to the second bone anchor. The first and second bone anchors can be positioned on the same side of the midline of the spine. The first and second vertebrae can be adjacent. The first and second vertebrae can be cervical vertebrae. The first vertebra can be C6 and the second vertebra can be C7. The first vertebra can be C6 and the second vertebra can be T1. The first vertebra can be C7 and the second vertebra can be T1. The superior surface can extend around at least 90 degrees of the perimeter of a head of the first bone anchor. The inferior surface can extend around at least 90 degrees of the perimeter of a head of the second bone anchor. Positioning the connector can include threading the first rod into a first recess in the connector and applying torque to a first drive interface of the connector to tighten the first rod to the connector. Positioning the connector can include attaching the first and second rods to the connector, the first and second rods having different diameters.

In some embodiments, a unitary spinal implant includes a first rod having a first diameter D1; a second rod having a second diameter D2, the second rod having an offset OC from the first rod; and a bent portion connecting the first and second rods, the bent portion having a length L defined by a distance between a first end and a second end of the bent portion, wherein a diameter of the bent portion is different from the first diameter D1 and the second diameter D2.

The diameter of the bent portion can include a diameter at the first end D3' and a diameter at the second end D3", the bent portion tapering continuously from D3' to D3". The bent portion can include a bending radius BR and a transition portion having a transition radius TR, the transition radius TR being equal to the bending radius BR.

BRIEF DESCRIPTION OF THE DRAWINGS

The following detailed description is provided with the accompanying drawings, in which.

DETAILED DESCRIPTION

Devices and methods that allow a rod to be offset in a relatively small amount of space are disclosed herein. In some embodiments, first and second offset rods can be joined by a plate-type connector having a reduced thickness suitable for insertion into a small space, e.g., between adjacent bone anchors. In some embodiments, first and second offset rods can be joined by a curved connector that conforms to adjacent bone anchors and likewise has a reduced thickness.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Figure 1A:
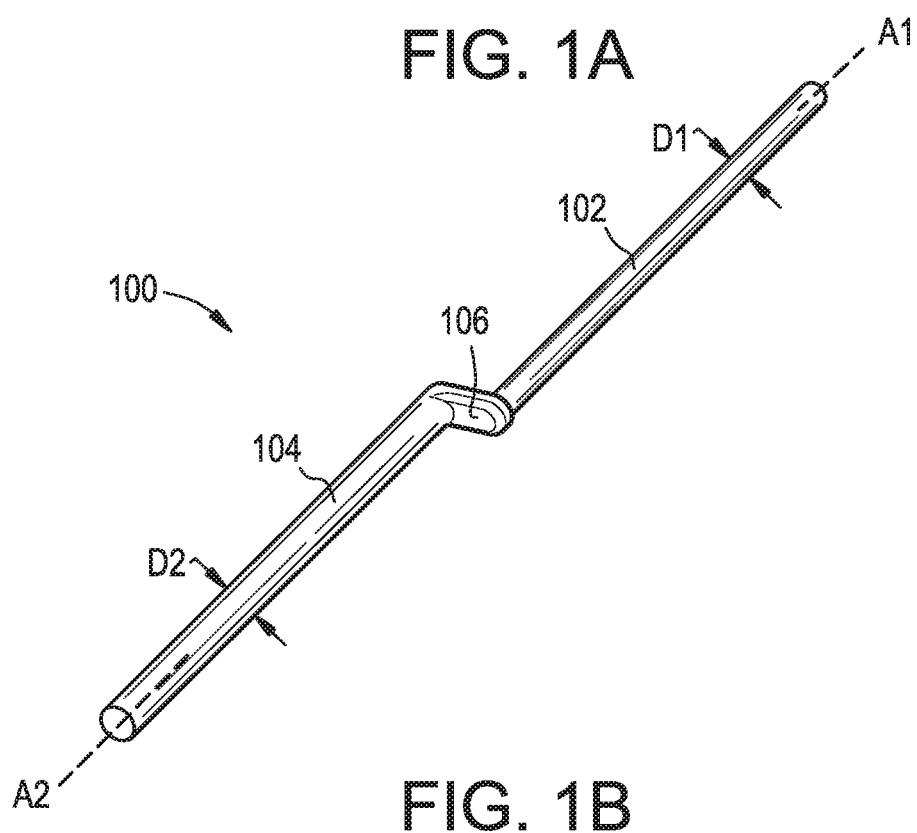
FIG. 1A is a perspective view of an implant that includes laterally-offset rods joined by a connector.
Figure 1B:
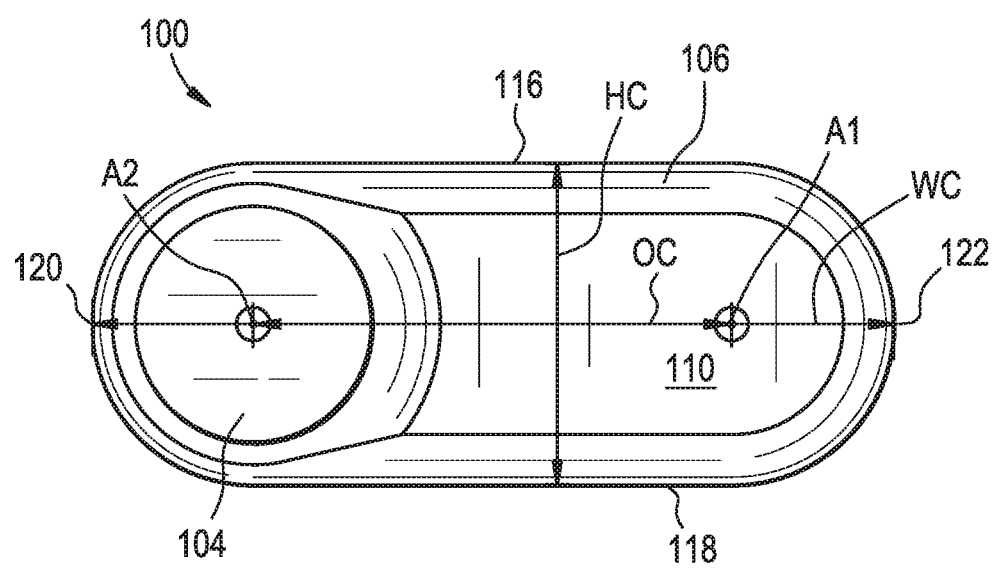
FIG. 1B is an end view of the implant of FIG. 1A.
Figure 1C:
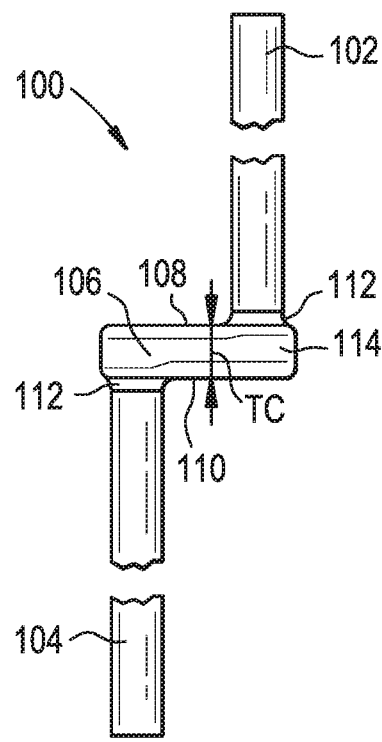
FIG. 1C is a top view of the implant of FIG. 1A.
Figure 1D:
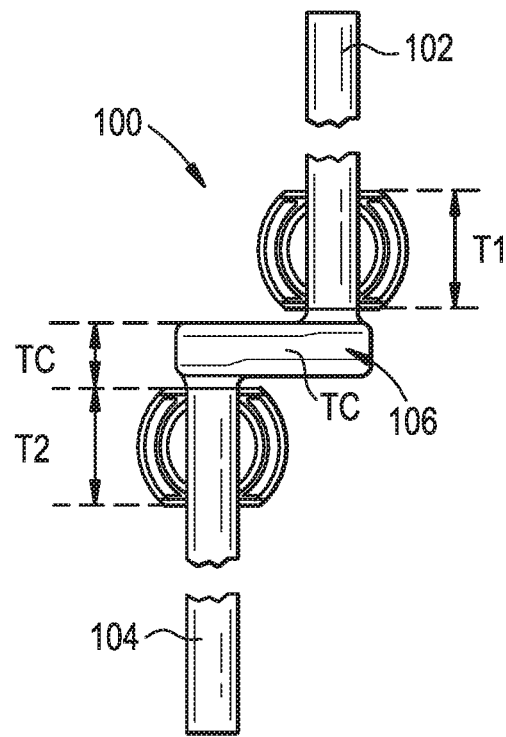
FIG. 1D is a top view of the implant of FIG. 1A, shown with first and second bone anchors.
Figure 1E:
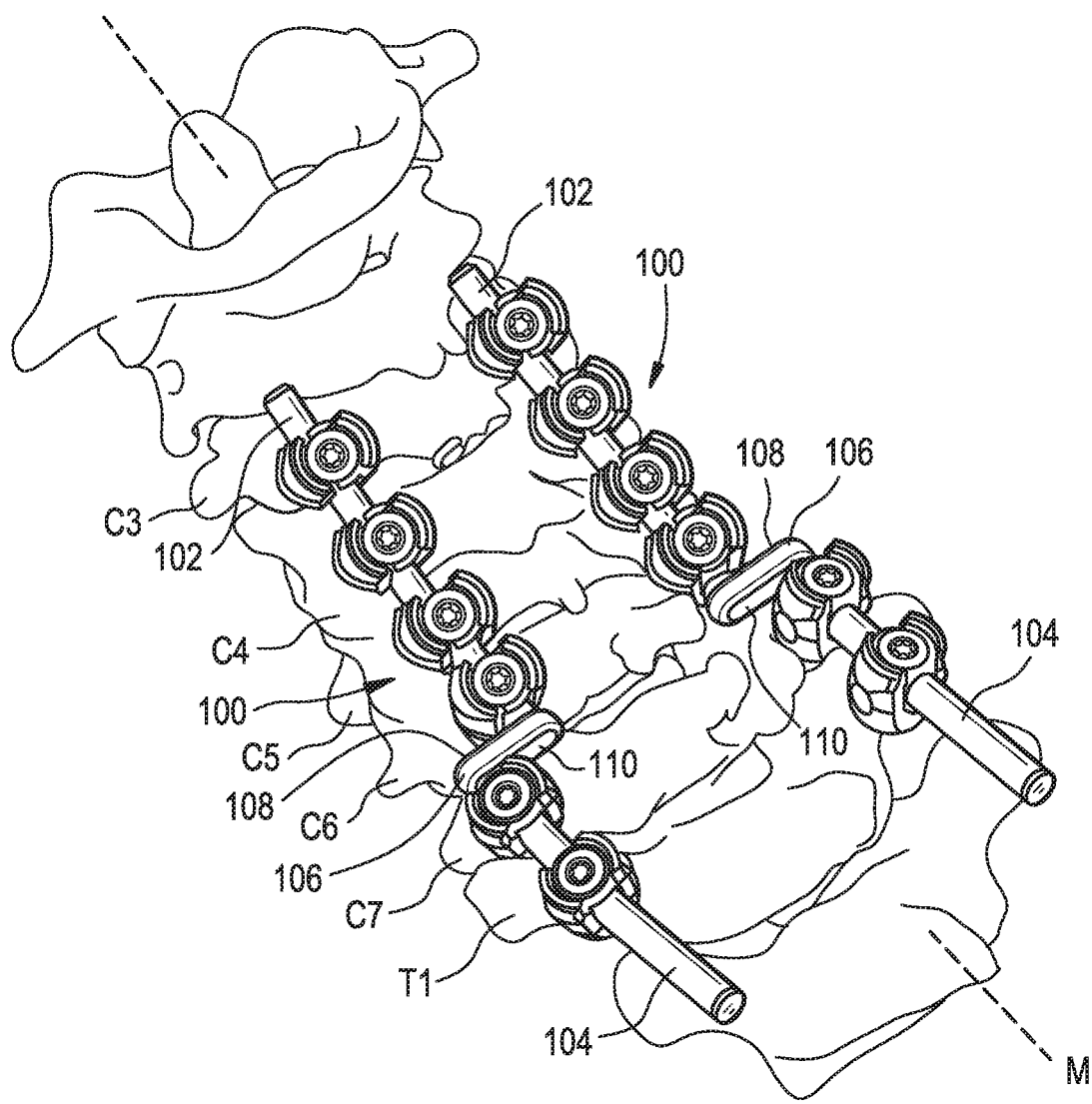
FIG. 1E is a perspective view of the implant of FIG. 1A secured to a spine.

FIGS. 1A-1E illustrate an exemplary embodiment of an implant 100 which can be used, for example, to connect offsetting bone anchors. As shown, the implant 100 can include a first rod 102, a second rod 104, and a connector 106 that connects the first and second rods 102, 104. The rods 102, 104 and the connector 106 can be a single monolithic unit as shown, or can be separate components permanently or temporarily joined to one another. For example, the first and second rods 102, 104 can be welded or permanently affixed to the connector 106 during manufacturing, or can be selectively coupled to the connector via a mating interface such as a threaded, keyed, pinned, snap-fit, or interference-fit connection, or combinations thereof. The connector 106 can provide a lateral offset or shift between the first rod 102 and the second rod 104. In use, as shown in FIG. 1E, the first and second rods 102, 104 can be secured to respective first and second bone anchors implanted in a patient, e.g., in vertebrae of the patient's spine, with the connector 106 being disposed between the bone anchors.

The low profile nature of the connector 106 can allow the offset connection between the rods 102, 104 to fit in a relatively small space. For example, the connector 106 can fit between bone anchors implanted in adjacent vertebrae, even when the adjacent vertebrae are very closely-spaced, such as the cervical vertebrae or the vertebrae of pediatric or small patients. This can obviate the need for the construct to skip over a vertebral level at the location of the offset, as is typically required with existing offset rods and tandem rod-to-rod connectors. Securing the construct without skipping over a level can, at least in some embodiments, improve the strength or stability of the construct. While it can be advantageous to avoid skipping levels, the methods and devices herein do not require that to be the case.

In the illustrated embodiment, the first and second rods 102, 104 are elongate cylindrical spinal rods, though it will be appreciated that the first and second rods can take other forms, such as bone plates, wires, tethers, and the like. It will also be appreciated that, while the illustrated rods 102, 104 have a circular cross-section, any of a variety of cross-sections can be used such as oval, oblong, square, rectangular, triangular, hexagonal, and so forth. The first rod 102 can have a diameter D1 and a central longitudinal axis A1. The second rod 104 can have a diameter D2 and a central longitudinal axis A2. When implanted in a patient, the longitudinal axes A1, A2 can be offset from one another in one or more planes, e.g., in a coronal plane, in a sagittal plane, or in both coronal and sagittal planes of the patient.

The first and second rods 102, 104 can have any of a variety of diameters D1, D2. In some embodiments, the diameters D1, D2 can range from 2.5 mm to 7.5 mm. For example, the diameters D1, D2 can be about 2.5 mm, about 3.0 mm, about 3.5 mm, about 4.0 mm, about 4.5 mm, about 4.75 mm, about 5.0 mm, about 5.5 mm, about 6.0 mm, about 6.35 mm, about 6.5 mm, about 7.0 mm, or about 7.5 mm. It will be appreciated that the diameter D1 of the first rod 102 can be less than, equal to, or greater than the diameter D2 of the second rod, as shown for example in FIG. 1A in which the first rod 102 has a lesser diameter than the second rod 104.

The first and second rods 102, 104 can be substantially straight along their length, or can include one or more bends or curves formed therein. The first and second rods 102, 104 can be malleable or bendable such that they can be bent before or during a procedure to achieve a desired shape, e.g., to achieve a desired correction or a desired curvature to conform to the lordosis or kyphosis of the spine.

The connector 106 can include a superior surface 108 and an inferior surface 110 from which the first and second rods 102, 104 respectively extend. While the rods 102, 104 are shown terminating at the connector 106, in some embodiments one or both of the rods can extend completely through the connector. The first and second rods 102, 104 can extend from the connector 106 in opposite directions as shown, though in other configurations the first and second rods can extend in the same direction, perpendicularly, or at an oblique angle from one another. The connector 106 can include flanges or gussets 112 where the rods 102, 104 meet the connector. The flanges 112 can provide additional strength to the joints between the rods 102, 104 and the connector 106.

In embodiments in which the rods 102, 104 and the connector 106 are separate components, the connector can include first and second recesses in which the rods are respectively received. As noted above, the rods 102, 104 can be welded or otherwise permanently secured within the recesses. The diameter of the recesses can correspond to that of the rod 102, 104 to which the connector 106 is to be coupled, though it will be appreciated that the diameter of the recesses can be the same, independent of the rod diameters to which the connector is coupled, and the rods can include a standard-sized mating end to mate with each recess. The recesses can be formed on opposite surfaces of the connector 106, or on the same surface of the connector. The recesses can extend completely through the connector 106, e.g., from the superior surface 108 to the opposite inferior surface 110, or can terminate prior to reaching the opposite surface.

The superior and inferior surfaces 108, 110 of the connector 106 can be connected by a sidewall 114 having a posterior portion 116, an anterior portion 118, and opposed lateral portions 120, 122. One or more portions of the sidewall 114 can be curved or tapered, e.g., to form an atraumatic shape or to provide clearance for anatomy or implants. For example, as shown, the lateral portions 120, 122 of the sidewall 114 can each form a section of a cylinder. As also shown, the intersections between the sidewall 114 and the superior and inferior surfaces 108, 110 can be convexly curved.

The connector 106 can define a width WC extending between the opposed lateral extents of the sidewall 114, a height HC extending between the anterior and posterior extents of the sidewall, and a thickness TC extending between the superior and inferior surfaces 108, 110. The connector 106 can also define an offset OC measured between the central axis A1 of the first rod 102 where the first rod meets the connector and the central axis A2 of the second rod 104 where the second rod meets the connector. The offset OC can be parallel to the width direction of the connector 106 as shown, or can extend obliquely relative to the width direction. In other words, the rods 102, 104 can be offset in both the width direction and the height direction of the connector 106.

The thickness TC of the connector 106 can vary based on factors such as the diameter of the rods 102, 104, the spacing between bone anchors with which the implant 100 is to be used, the size of bone anchors with which the implant is to be used, anatomical dimensions of the patient, and so forth. The thickness TC can be selected to be small enough to fit between adjacent bone anchors but large enough to withstand anatomical forces to which the connector 106 is likely to be subjected post-implantation.

The thickness TC can be in the range of 0.5 mm to 8 mm, in the range of 1 mm to 5 mm, and/or in the range of 2 mm to 4 mm. The thickness TC can be about 3.5 mm.

The thickness TC can be about 8 mm, about 7.5 mm, about 7.0 mm, about 6.5 mm, about 6.0 mm, about 5.5 mm, about 5.0 mm, about 4.5 mm, about 4.0 mm, about 3.5 mm, about 3.0 mm, about 2.5 mm, about 2.0 mm, about 1.5 mm, about 1.0 mm, and/or about 0.5 mm.

The thickness TC can be less than about 8 mm, less than about 7 mm, less than about 6 mm, less than about 5 mm, less than about 4 mm, less than about 3 mm, less than about 2 mm, and/or less than about 1 mm.

The thickness TC can be less than, equal to, or greater than the diameter D1 of the first rod 102. The ratio between the thickness TC and the diameter D1 can be in the range of 0.05 to 3.0, in the range of 0.25 to 1, and/or in the range of 0.5 to 0.75. The ratio between the thickness TC and the diameter D1 can be about 3.0, about 2.5, about 2.0, about 1.0, about 0.75, about 0.5, about 0.25, about 0.1, and/or about 0.05. The ratio between the thickness TC and the diameter D1 can be less than about 3.0, less than about 2.5, less than about 2.0, less than about 1.0, less than about 0.75, less than about 0.5, less than about 0.25, less than about 0.1, and/or less than about 0.05.

The thickness TC can be less than, equal to, or greater than the diameter D2 of the second rod 104. The ratio between the thickness TC and the diameter D2 can be in the range of 0.05 to 3.0, in the range of 0.25 to 1, and/or in the range of 0.5 to 0.75. The ratio between the thickness TC and the diameter D2 can be about 3.0, about 2.5, about 2.0, about 1.0, about 0.75, about 0.5, about 0.25, about 0.1, and/or about 0.05. The ratio between the thickness TC and the diameter D2 can be less than about 3.0, less than about 2.5, less than about 2.0, less than about 1.0, less than about 0.75, less than about 0.5, less than about 0.25, less than about 0.1, and/or less than about 0.05.

The thickness TC can be less than, equal to, or greater than a corresponding thickness dimension T1 of the head portion of a first bone anchor in which the first rod 102 is disposed. The first bone anchor can be positioned adjacent to and/or in contact with the superior surface 108 of the connector 106. The ratio between the thickness TC and the thickness T1 can be in the range of 0.04 to 1.3, in the range of 0.33 to 0.75, and/or in the range of 0.4 to 0.6. The ratio between the thickness TC and the thickness T1 can be about 1.3, about 1.0, about 0.75, about 0.6, about 0.5, about 0.4, about 0.33, about 0.25, about 0.1, and/or about 0.04. The ratio between the thickness TC and the thickness T1 can be less than about 1.3, less than about 1.0, less than about 0.75, less than about 0.6, less than about 0.5, less than about 0.25, less than about 0.1, and/or less than about 0.04.

The thickness TC can be less than, equal to, or greater than a corresponding thickness dimension T2 of the head portion of a second bone anchor in which the second rod 104 is disposed. The second bone anchor can be positioned adjacent to and/or in contact with the inferior surface 110 of the connector 106. The ratio between the thickness TC and the thickness T2 can be in the range of 0.04 to 1.3, in the range of 0.33 to 0.75, and/or in the range of 0.4 to 0.6. The ratio between the thickness TC and the thickness T2 can be about 1.3, about 1.0, about 0.75, about 0.6, about 0.5, about 0.4, about 0.33, about 0.25, about 0.1, and/or about 0.04. The ratio between the thickness TC and the thickness T2 can be less than about 1.3, less than about 1.0, less than about 0.75, less than about 0.6, less than about 0.5, less than about 0.25, less than about 0.1, and/or less than about 0.04.

The thickness TC can be less than, equal to, or greater than the offset OC of the connector 106. The ratio between the thickness TC and the offset OC can be in the range of 0.05 to 2.0, in the range of 0.25 to 1, and/or in the range of 0.5 to 0.75. The ratio between the thickness TC and the offset OC can be about 2.0, about 1.0, about 0.75, about 0.5, about 0.25, about 0.1, and/or about 0.05. The ratio between the thickness TC and the offset OC can be less than about 2.0, less than about 1.0, less than about 0.75, less than about 0.5, less than about 0.25, less than about 0.1, and/or less than about 0.05.

The thickness TC can be less than or equal to a distance in the coronal plane between an inferior-most extent of a first bone anchor implanted in a first vertebra and a superior-most extent of a second bone anchor implanted in a second vertebra, the second vertebra being inferior to the first vertebra and adjacent to the first vertebra.

An implant 100 having the above dimensions can overcome space constraints for securing an implant between adjacent offsetting bone anchors while also providing a secure connection with rods disposed in those bone anchors.

The rods 102, 104 and the connector 106 can be formed from rigid or malleable materials, including metals such as titanium, titanium alloys, cobalt chromium, or stainless steel, polymers such as PEEK, ceramics, fibers such as carbon fiber, any of a variety of materials suitable for use in surgical implants, and combinations thereof.

In use, the implant 100 can be coupled to one or more bone anchors to secure the implant to a bone structure of a patient. For example, as shown in FIG. 1E, the implant 100 can be coupled to a plurality of bone anchors implanted in the spine of a patient such that the first and second rods 102, 104 extend longitudinally along the spine. Multiple implants 100 can be secured to the spine, e.g., one on each side of the midline M of the spine as shown. The implants 100 can be secured to the posterior aspects of the spine, e.g., using bone anchors implanted in the pedicle, lateral mass, or lamina of each vertebra, or in the lateral or anterior aspects of the spine.

In the illustrated construct, four superior vertebrae C3, C4, C5, C6 are instrumented with bilateral lateral mass screws and two inferior vertebrae C7, T1 are instrumented with bilateral pedicle screws. A lateral offset exists between the rod slots of the lateral mass screws implanted in C6 and the pedicle screws implanted in C7. Accordingly, the connector 106 of the implant 100 can be positioned as shown between C6 and C7 to provide a lateral offset between the first rod 102 disposed in the superior lateral mass screws and the second rod 104 disposed in the inferior pedicle screws. The connector 106 can be positioned such that the superior surface 108 contacts the head portion of a superior bone anchor and such that the inferior surface 110 contacts the head portion of an inferior bone anchor, the superior and inferior bone anchors being implanted in adjacent vertebrae.

It will be appreciated that the arrangement shown is merely exemplary, and that any number of implants 100 or bone anchors can be used at any level of the spine.

Once the desired orientation of the implant 100 and the patient anatomy is achieved, the rods 102, 104 can be fixed in place by set screws or other closure mechanisms secured to the bone anchors. It will be appreciated that the implant 100 can be used with any of a variety of bone anchors, including those shown in FIG. 1E, the exemplary prior art bone anchor described below and shown in FIGS. 4A-4B, or any other suitable bone anchor.

Figure 2A:
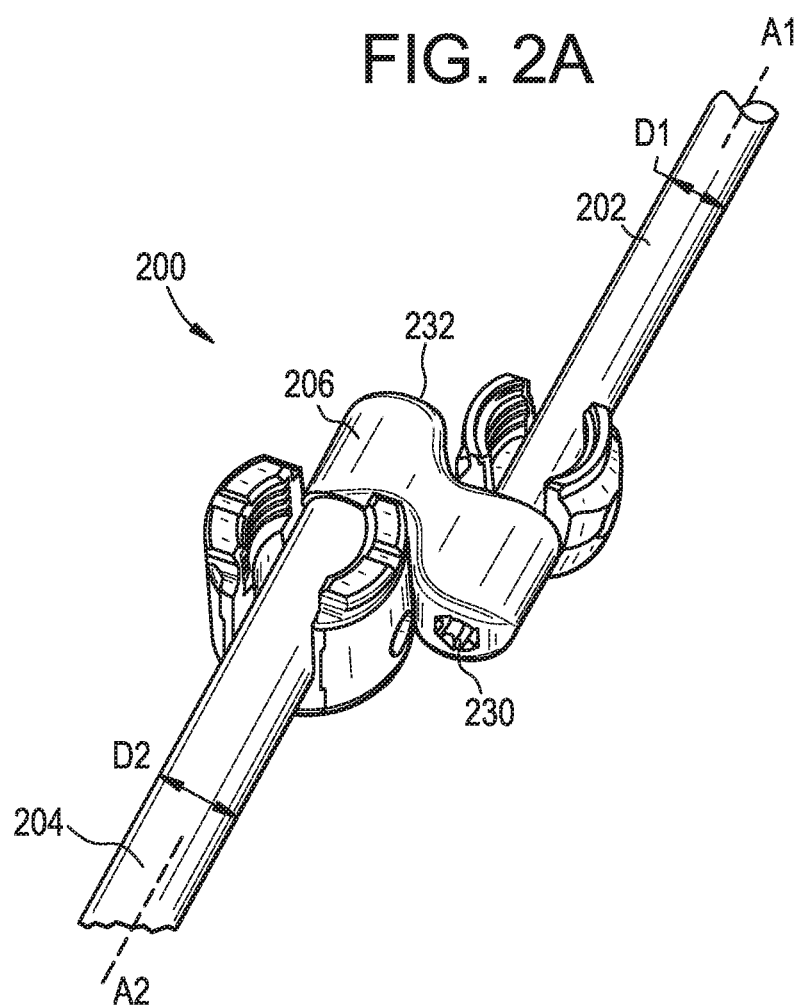
FIG. 2A is a perspective view of another implant that includes laterally-offset rods joined by a connector, shown with first and second bone anchors.
Figure 2B:
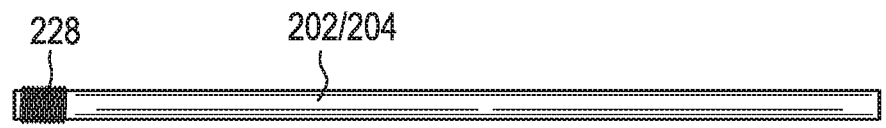
FIG. 2B is a top view of a threaded rod that can be used with the implant of FIG. 2A.
Figure 2C:
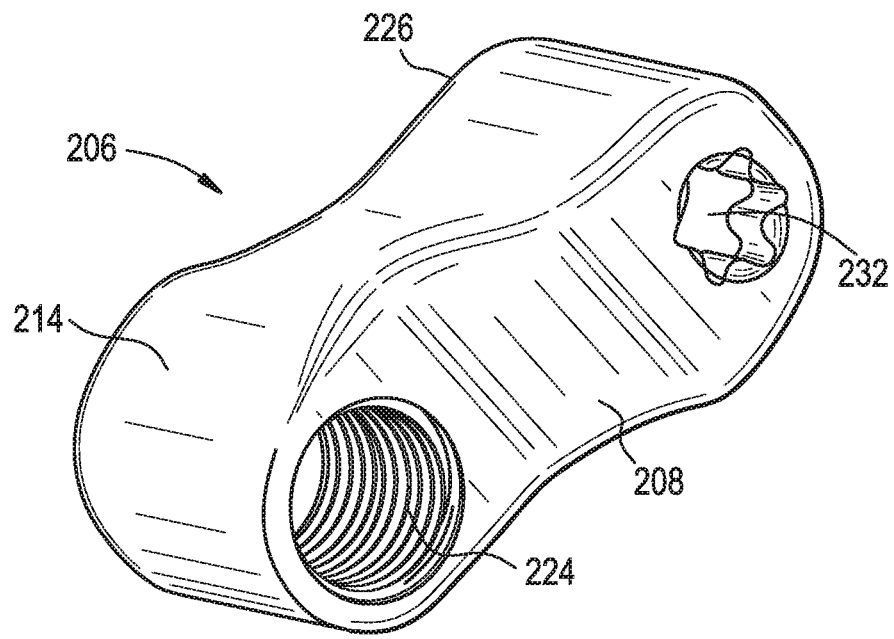
FIG. 2C is a perspective view of the connector of the implant of FIG. 2A.
Figure 2D:
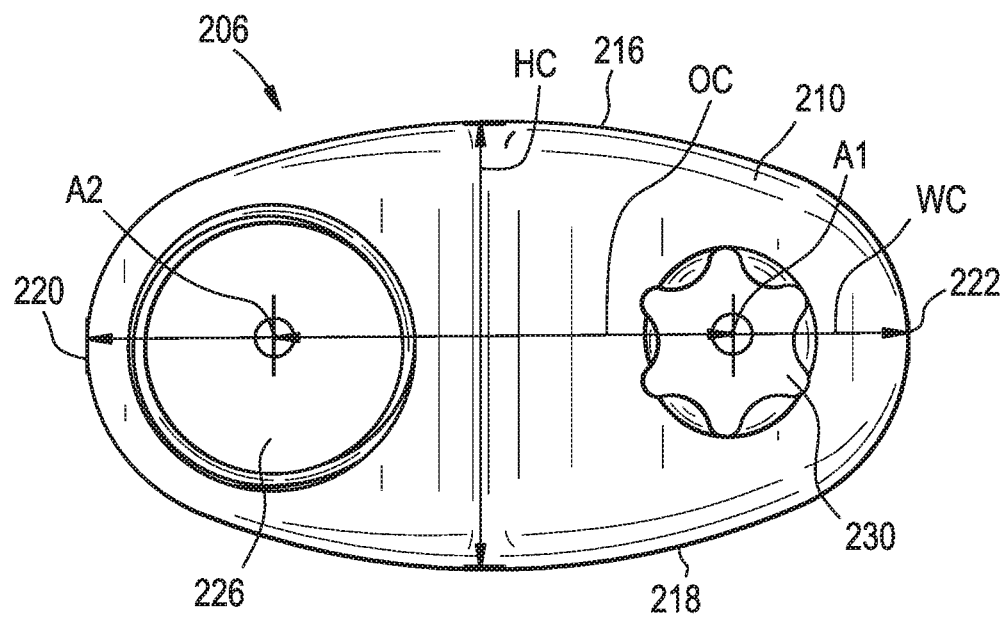
FIG. 2D is an end view of the connector of the implant of FIG. 2A.
Figure 2E:
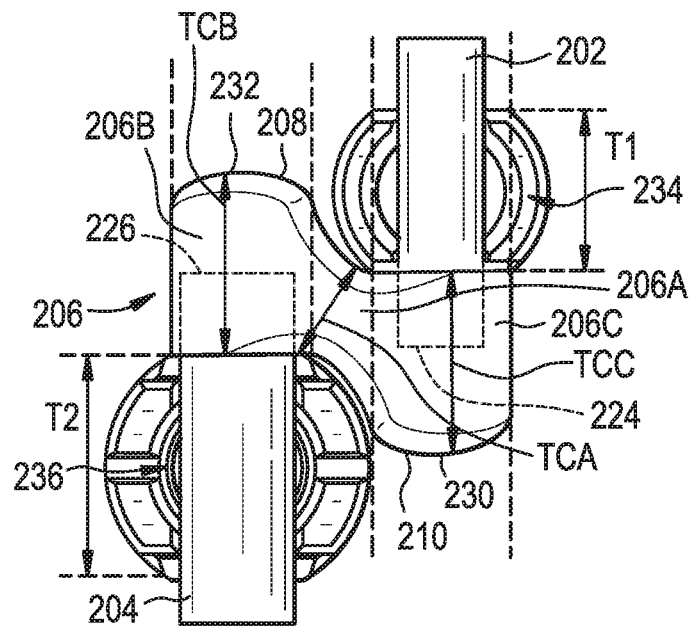
FIG. 2E is a top view of the implant and bone anchors of FIG. 2A.
Figure 2F:
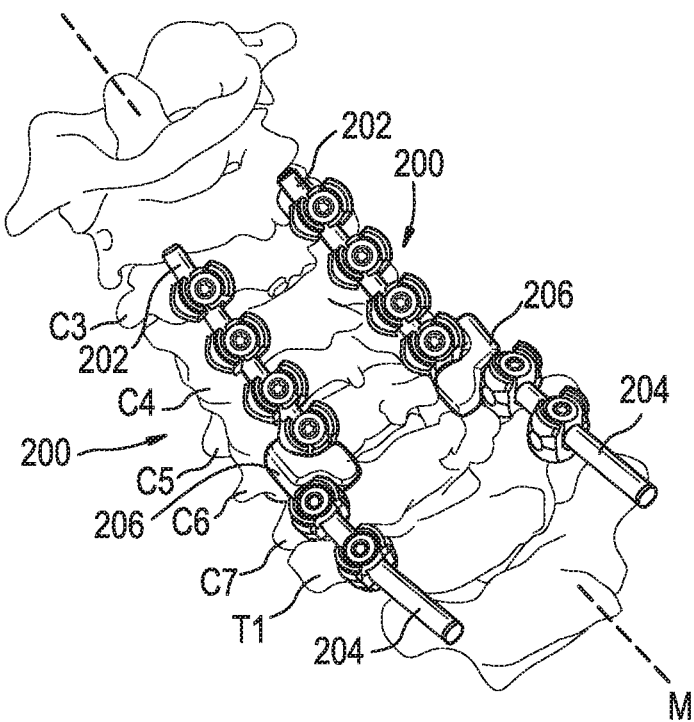
FIG. 2F is a perspective view of the implant of FIG. 2A secured to a spine.

FIGS. 2A-2F illustrate another exemplary embodiment of an implant 200 which can be used, for example, to connect offsetting bone anchors. As shown, the implant 200 can include a first rod 202, a second rod 204, and a connector 206 that connects the first and second rods. The rods 202, 204 can be selectively coupled to the connector 206, e.g., using a threaded connection as shown, or can be permanently coupled to the connector or formed as a single monolithic unit with the connector. For example, the first and second rods 202, 204 can be welded or permanently affixed to the connector 206 during manufacturing. While a threaded connection is shown, the rods 202, 204 can also be coupled to the connector 206 using a keyed, pinned, snap-fit, interference-fit, or other connection. The connector 206 can provide a lateral offset or shift between the first rod 202 and the second rod 204. In use, as shown in FIG. 2F, the first and second rods 202, 204 can be secured to respective first and second bone anchors implanted in a patient, e.g., in vertebrae of the patient's spine, with the connector 206 being disposed between the bone anchors.

The low profile nature of the connector 206 can allow the offset connection between the rods 202, 204 to fit in a relatively small space. For example, the connector 206 can fit between bone anchors implanted in adjacent vertebrae, even when the adjacent vertebrae are very closely-spaced, such as the cervical vertebrae or the vertebrae of pediatric or small patients. This can obviate the need for the construct to skip over a vertebral level at the location of the offset, as is typically required with existing offset rods and tandem rod-to-rod connectors. Securing the construct without skipping over a level can, at least in some embodiments, improve the strength or stability of the construct. While it can be advantageous to avoid skipping levels, the methods and devices herein do not require that to be the case.

In the illustrated embodiment, the first and second rods 202, 204 are elongate cylindrical spinal rods, though it will be appreciated that the first and second rods can take other forms, such as bone plates, wires, tethers, and the like. It will also be appreciated that, while the illustrated rods 202, 204 have a circular cross-section, any of a variety of cross-sections can be used such as oval, oblong, square, rectangular, triangular, hexagonal, and so forth. The first rod 202 can have a diameter D1 and a central longitudinal axis A1. The second rod 204 can have a diameter D2 and a central longitudinal axis A2. When implanted in a patient, the longitudinal axes A1, A2 can be offset from one another in one or more planes, e.g., in a coronal plane, in a sagittal plane, or in both coronal and sagittal planes of the patient.

The first and second rods 202, 204 can have any of a variety of diameters D1, D2. In some embodiments, the diameters D1, D2 can range from 2.5 mm to 7.5 mm. For example, the diameters D1, D2 can be about 2.5 mm, about 3.0 mm, about 3.5 mm, about 4.0 mm, about 4.5 mm, about 4.75 mm, about 5.0 mm, about 5.5 mm, about 6.0 mm, about 6.35 mm, about 6.5 mm, about 7.0 mm, or about 7.5 mm. It will be appreciated that the diameter D1 of the first rod 202 can be less than, equal to, or greater than the diameter D2 of the second rod 204, as shown for example in FIG. 2A in which the second rod 204 has a greater diameter than the first rod 202.

The first and second rods 202, 204 can be substantially straight along their length, or can include one or more bends or curves formed therein. The first and second rods 202, 204 can be malleable or bendable such that they can be bent before or during a procedure to achieve a desired shape, e.g., to achieve a desired correction or a desired curvature to conform to the lordosis or kyphosis of the spine.

The connector 206 can include a superior surface 208 and an inferior surface 210 from which the first and second rods 202, 204 respectively extend. While the rods 202, 204 are shown terminating at the connector 206, in some embodiments one or both of the rods can extend completely through the connector. The first and second rods 202, 204 can extend from the connector in opposite directions as shown, though in other configurations the first and second rods can extend in the same direction, perpendicularly, or at an oblique angle from one another. The connector 206 can include flanges or gussets (not shown) where the rods 202, 204 meet the connector. The flanges can provide additional strength to the joints between the rods 202, 204 and the connector 206.

The connector 206 can include a central portion 206A that extends between opposed lateral portions 206B, 206C.

In embodiments in which the rods 202, 204 and the connector 206 are separate components, the connector can include first and second recesses 224, 226 in which the rods are respectively received. The first recess 224 can be formed in one lateral portion 206C of the connector and the second recess can 226 be formed in the opposite lateral portion 206B. As noted above, the rods 202, 204 can be welded or otherwise permanently secured within the recesses 224, 226. The diameter of the recesses 224, 226 can correspond to that of the rod to which the connector 206 is to be coupled, though it will be appreciated that the diameter of the recesses can be the same, independent of the rod diameters to which the connector is coupled, and the rods can include a standard-sized mating end to mate with each recess. The recesses 224, 226 can be formed on opposite surfaces of the connector 206, or on the same surface of the connector. The recesses 224, 226 can extend completely through the connector, e.g., from the superior surface 208 to the opposite inferior surface 210, or can terminate prior to reaching the opposite surface. As shown in FIG. 2B, each rod 202, 204 can include an externally-threaded feature 228 for selectively coupling the rod to a corresponding threaded recess 224, 226 of the connector 206. The threaded feature 228 can be formed at a terminal end of the rod as shown or at any location along the rod's length, e.g., at a midpoint of the rod.

The connector 206 can include one or more drive interfaces to facilitate application of torque or other forces to the connector, e.g., for coupling the connector to the rods 202, 204. In the illustrated embodiment, the connector 206 includes first and second drive interfaces 230, 232 that are axially aligned with and opposite to the first and second rod recesses 224, 226. In particular, the connector 206 includes a first drive interface 230 formed in the inferior surface 210 and in the first lateral portion 206C, a first rod recess 224 formed in the superior surface 208 and in the first lateral portion 206C, a second rod recess 226 formed in the inferior surface 210 and in the second lateral portion 206B, and a second drive interface 232 formed in the superior surface 208 and in the second lateral portion 206B. The drive interfaces 230, 232 can have any geometry that facilitates application of torque or other forces to the connector 206, e.g., for rotatably tightening the connector to the first and second rods 202, 204. A Torx or hexalobe drive interface is shown, though it will be appreciated that other drive types such as slotted, Phillips, square, Robertson, hex, pentalobe, etc. can be used instead or in addition.

The superior and inferior surfaces 208, 210 of the connector 206 can be connected by a sidewall 214 having a posterior portion 216, an anterior portion 218, and opposed lateral portions 220, 222. One or more portions of the sidewall 214 can be curved or tapered, e.g., to form an atraumatic shape or to provide clearance for anatomy or implants. For example, as shown, the posterior portion 216, the anterior portion 218, and the opposed lateral portions 220, 222 of the sidewall 214 can each have a cross-section that forms a section of an ellipse. In some embodiments, the connector 206 can have an elliptical cross-section. As also shown, the intersections between the sidewall 214 and the superior and inferior surfaces 208, 210 can be convexly curved.

The connector 206 can define a width WC extending between the opposed lateral extents of the sidewall 214, a height HC extending between the anterior and posterior extents of the sidewall 214, and a thickness TC extending between the superior and inferior surfaces 208, 210. The connector 206 can also define an offset OC measured between the central axis A1 of the first rod 202 where the first rod meets the connector and the central axis A2 of the second rod 204 where the second rod meets the connector. The offset OC can be parallel to the width direction of the connector 206 as shown, or can extend obliquely relative to the width direction. In other words, the rods 202, 204 can be offset in both the width direction and the height direction of the connector 206.

The thickness TC of the connector 206 can vary along the width WC of the connector. For example, in the illustrated embodiment, the central portion 206A of the connector has a thickness TC that varies with the contour of the superior and inferior surfaces 208, 210 to a minimum thickness TCA. The opposed lateral portions 206B, 206C of the connector each have a thickness TCB, TCC that is greater than the thickness TCA of the central portion 206A.

The connector 206 can thus include contoured superior and/or inferior surfaces 208, 210. The contour of the superior and inferior surfaces 208, 210 can be selected to conform or substantially conform to the exterior profile of one or more bone anchors or other implants with which the connector 206 is to be used. For example, as shown in FIG. 2E, the superior surface 208 of the connector can include a planar portion configured to abut or contact a corresponding planar portion of the head or receiver member of a superior bone anchor 234. The superior surface 208 can also include a concavely curved portion configured to abut or contact a corresponding convexly curved portion of the head or receiver member of the superior bone anchor 234. The superior surface 208 can include a convexly curved portion at an end opposite the planar portion, where the first drive interface 232 can be formed. The inferior surface 210 of the connector 206 can be similarly shaped. Accordingly, one or both of the superior and inferior surfaces 208, 210 of the connector 206 can conform to, nest with, provide a relief for, and/or form a negative of corresponding exterior surfaces of adjacent bone anchors 234, 236. In some embodiments, the superior and inferior surfaces 208, 210 closely track and/or make contact with the adjacent bone anchors 234, 236 along a portion of the exterior perimeter of the head of the bone anchor, e.g., along at least 45 degrees of the perimeter, along at least 60 degrees of the perimeter, along at least 75 degrees of the perimeter, along at least 90 degrees of the perimeter, and/or along at least 115 degrees of the perimeter. While the superior and inferior surfaces are shown with convex portions, those portions can alternatively be flat, counterbored, and so forth.

The thickness TCA of the central portion 206A of the connector 206 can vary based on factors such as the diameter of the rods 202, 204, the spacing between bone anchors with which the implant 200 is to be used, the size of bone anchors with which the implant is to be used, anatomical dimensions of the patient, and so forth. The thickness TCA can be selected to be small enough to fit between adjacent bone anchors but large enough to withstand anatomical forces to which the connector 206 is likely to be subjected post-implantation.

The thickness TCA can be in the range of 0.5 mm to 8 mm, in the range of 2 mm to 4 mm, and/or in the range of 2.5 mm to 3.5 mm.

The thickness TCA can be about 8 mm, about 7.5 mm, about 7.0 mm, about 6.5 mm, about 6.0 mm, about 5.5 mm, about 5.0 mm, about 4.5 mm, about 4.0 mm, about 3.5 mm, about 3.0 mm, about 2.5 mm, about 2.0 mm, about 1.5 mm, about 1.0 mm, and/or about 0.5 mm.

The thickness TCA can be less than about 8 mm, less than about 7 mm, less than about 6 mm, less than about 5 mm, less than about 4 mm, less than about 3 mm, less than about 2 mm, and/or less than about 1 mm.

The thickness TCA can be less than, equal to, or greater than the diameter D1 of the first rod 202. The ratio between the thickness TCA and the diameter D1 can be in the range of 0.05 to 3.0, in the range of 0.25 to 1, and/or in the range of 0.5 to 0.75. The ratio between the thickness TCA and the diameter D1 can be about 3.0, about 2.5, about 2.0, about 1.0, about 0.75, about 0.5, about 0.25, about 0.1, and/or about 0.05. The ratio between the thickness TCA and the diameter D1 can be less than about 3.0, less than about 2.5, less than about 2.0, less than about 1.0, less than about 0.75, less than about 0.5, less than about 0.25, less than about 0.1, and/or less than about 0.05.

The thickness TCA can be less than, equal to, or greater than the diameter D2 of the second rod 204. The ratio between the thickness TCA and the diameter D2 can be in the range of 0.05 to 3.0, in the range of 0.25 to 1, and/or in the range of 0.5 to 0.75. The ratio between the thickness TCA and the diameter D2 can be about 3.0, about 2.5, about 2.0, about 1.0, about 0.75, about 0.5, about 0.25, about 0.1, and/or about 0.05. The ratio between the thickness TCA and the diameter D2 can be less than about 3.0, less than about 2.5, less than about 2.0, less than about 1.0, less than about 0.75, less than about 0.5, less than about 0.25, less than about 0.1, and/or less than about 0.05.

The thickness TCA can be less than, equal to, or greater than a corresponding thickness dimension T1 of the head portion of a first bone anchor 234 in which the first rod 202 is disposed. The first bone anchor 234 can be positioned adjacent to and/or in contact with the superior surface 208 of the connector 206. The ratio between the thickness TCA and the thickness T1 can be in the range of 0.04 to 1.3, in the range of 0.33 to 0.75, and/or in the range of 0.4 to 0.6. The ratio between the thickness TCA and the thickness T1 can be about 1.3, about 1.0, about 0.75, about 0.6, about 0.5, about 0.4, about 0.33, about 0.25, about 0.1, and/or about 0.04. The ratio between the thickness TCA and the thickness T1 can be less than about 1.3, less than about 1.0, less than about 0.75, less than about 0.6, less than about 0.5, less than about 0.25, less than about 0.1, and/or less than about 0.04.

The thickness TCA can be less than, equal to, or greater than a corresponding thickness dimension T2 of the head portion of a second bone anchor 236 in which the second rod 204 is disposed. The second bone anchor 236 can be positioned adjacent to and/or in contact with the inferior surface 210 of the connector 206. The ratio between the thickness TCA and the thickness T2 can be in the range of 0.04 to 1.3, in the range of 0.33 to 0.75, and/or in the range of 0.4 to 0.6. The ratio between the thickness TCA and the thickness T2 can be about 1.3, about 1.0, about 0.75, about 0.6, about 0.5, about 0.4, about 0.33, about 0.25, about 0.1, and/or about 0.04. The ratio between the thickness TCA and the thickness T2 can be less than about 1.3, less than about 1.0, less than about 0.75, less than about 0.6, less than about 0.5, less than about 0.25, less than about 0.1, and/or less than about 0.04.

The thickness TCA can be less than, equal to, or greater than the offset OC of the connector 206. The ratio between the thickness TCA and the offset OC can be in the range of 0.05 to 2.0, in the range of 0.25 to 1, and/or in the range of 0.5 to 0.75. The ratio between the thickness TCA and the offset OC can be about 2.0, about 1.0, about 0.75, about 0.5, about 0.25, about 0.1, and/or about 0.05. The ratio between the thickness TCA and the offset OC can be less than about 2.0, less than about 1.0, less than about 0.75, less than about 0.5, less than about 0.25, less than about 0.1, and/or less than about 0.05.

The thickness TCA can be less than or equal to a distance in the coronal plane between an inferior-most extent of a first bone anchor implanted in a first vertebra and a superior-most extent of a second bone anchor implanted in a second vertebra, the second vertebra being inferior to the first vertebra and adjacent to the first vertebra.

An implant having the above dimensions can overcome space constraints for securing an implant 200 between adjacent offsetting bone anchors while also providing a secure connection with rods disposed in those bone anchors.

The rods 202, 204 and the connector 206 can be formed from rigid or malleable materials, including metals such as titanium, titanium alloys, cobalt chromium, or stainless steel, polymers such as PEEK, ceramics, fibers such as carbon fiber, any of a variety of materials suitable for use in surgical implants, and combinations thereof.

In use, the implant 200 can be coupled to one or more bone anchors to secure the implant to a bone structure of a patient. For example, as shown in FIG. 2F, the implant 200 can be coupled to a plurality of bone anchors implanted in the spine of a patient such that the first and second rods 202, 204 extend longitudinally along the spine. Multiple implants 200 can be secured to the spine, e.g., one on each side of the midline M of the spine as shown. The implants 200 can be secured to the posterior aspects of the spine, e.g., using bone anchors implanted in the pedicle, lateral mass, or lamina of each vertebra, or in the lateral or anterior aspects of the spine.

In the illustrated construct, four superior vertebrae C3, C4, C5, C6 are instrumented with bilateral lateral mass screws and two inferior vertebrae C7, T1 are instrumented with bilateral pedicle screws. A lateral offset exists between the lateral mass screws implanted in C6 and the pedicle screws implanted in C7. Accordingly, the connector 206 of the implant 200 can be positioned as shown between C6 and C7 to provide a lateral offset between the first rod 202 disposed in the superior lateral mass screws and the second rod 204 disposed in the inferior pedicle screws. The connector 206 can be positioned such that the superior surface 208 contacts the head portion of a superior bone anchor and such that the inferior surface 210 contacts the head portion of an inferior bone anchor, the superior and inferior screws being implanted in adjacent vertebrae.

It will be appreciated that the arrangement shown is merely exemplary, and that any number of implants 200 or bone anchors can be used at any level of the spine.

Once the desired orientation of the implant 200 and the patient anatomy is achieved, the rods 202, 204 can be fixed in place by set screws or other closure mechanisms secured to the bone anchors. It will be appreciated that the implant 200 can be used with any of a variety of bone anchors, including those shown in FIG. 2F, the exemplary prior art bone anchor described below and shown in FIGS. 4A-4B, or any other suitable bone anchor.

FIGS. 3A-3D illustrate another exemplary embodiment of an implant 300 which can be used, for example, to connect offsetting bone anchors. Except as indicated below and as will be readily appreciated by one having ordinary skill in the art, the structure and operation of the implant 300 is substantially similar to that of the implants 100, 200 described above and therefore a detailed description is omitted here for the sake of brevity.

Figure 3A:
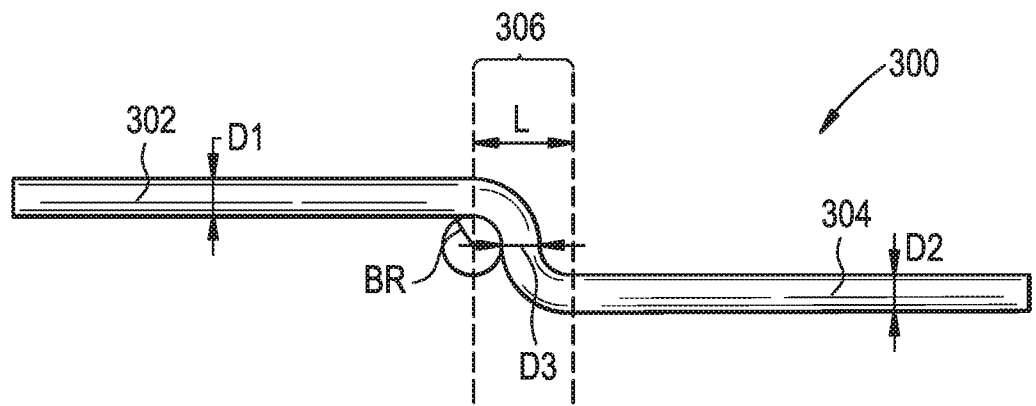
FIG. 3A is a top view of another implant that includes laterally-offset rods joined by a connector.
Figure 3B:
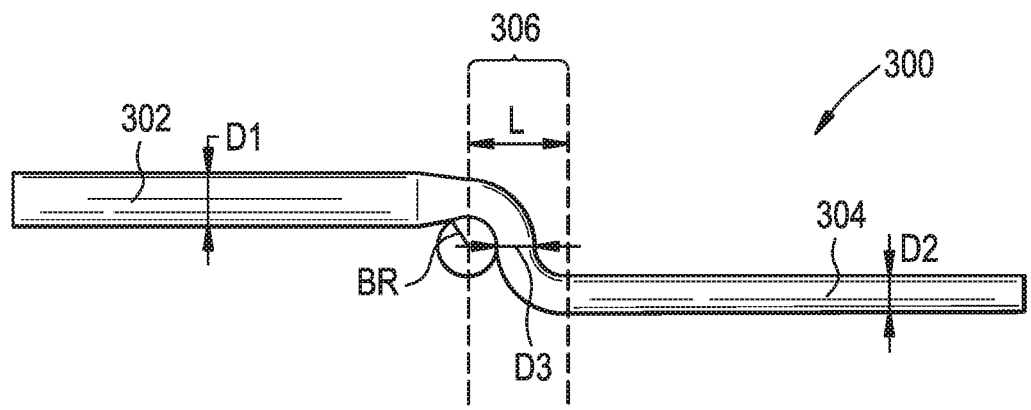
FIG. 3B is a top view of the implant of FIG. 3A with first and second rods having different diameters.

As shown, the implant 300 can include first and second rods 302, 304 and a connector 306 formed by an integral bent portion of the first and second rods. The rods 302, 304 can be selectively coupled to the connector 306, or can be permanently coupled to the connector or formed as a single monolithic unit with the connector. The first and second rods 302, 304 and the bent portion 306 can have the same diameter as shown in FIG. 3A, or can have different diameters as shown in FIG. 3B. The bent portion 306 can have a diameter D3 that is less than the diameter D1 of the first rod 302 and less than the diameter D2 of the second rod 304. The low profile nature of the bent portion 306 can allow the offset connection between the rods 302, 304 to fit in a relatively small space.

Figure 3C:
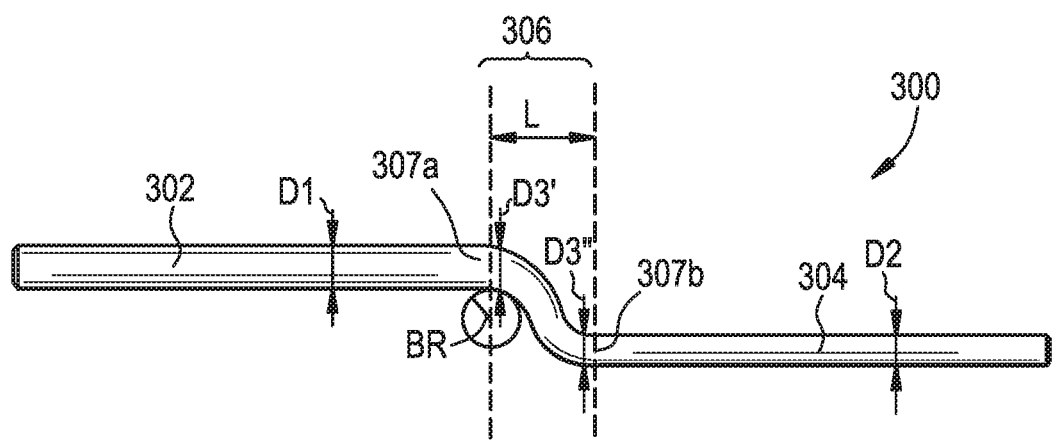
FIG. 3C is a top view of the implant of FIG. 3A with the implant transitioning from one diameter to another in a bent portion.
Figure 3D:
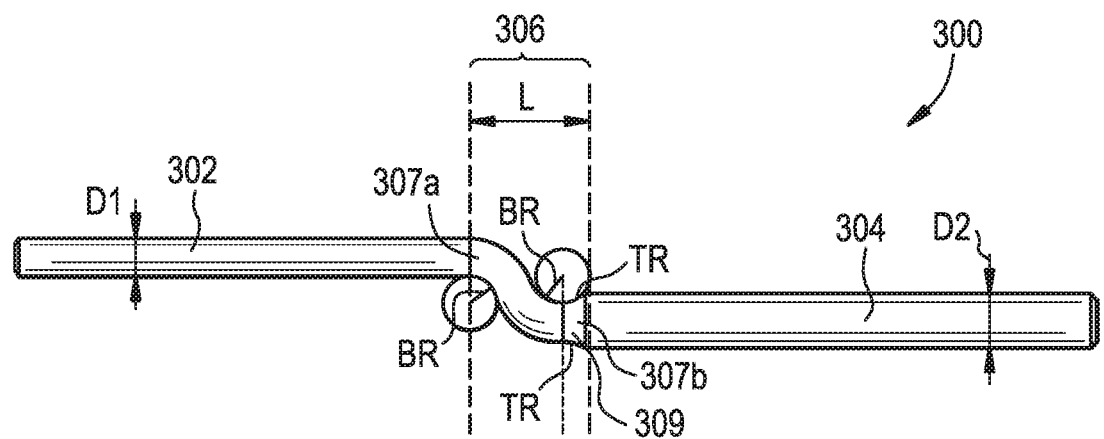
FIG. 3D is a top view of the implant of FIG. 3A with a bent portion and a transition portion.

In some embodiments, as shown in FIGS. 3C-3D, the change in diameter between the first rod 302 and the second rod 304 occurs in the bent portion 306. The bent portion 306 can include a first end 307a and a second end 307b having a length L therebetween. It will be appreciated that the diameter D3 can be uniform throughout its length, or, as shown in FIG. 3C, the first end 307a can include a first diameter D3' and the second end 307b can include a second diameter D3". The first diameter D3' can be larger or smaller than the second diameter D3". The bent portion 306 can taper continuously from the first diameter D3' to the second diameter D3". In other words, the diameter of the bent portion 306 can progressively decrease along the length L of the bent portion.

The bent portion 306 can include a bending radius BR which, as shown, can be the radius of curvature of the bent portion 306 at the first and/or second ends 307a, 307b. The value of the bending radius BR can vary based on factors such as the diameter of the rods 302, 304, the proximity of adjacent bone anchors, and so forth. The value of the bending radius BR can be in the range of 1.5 mm to 6.0 mm, in the range of 2.0 mm to 3.0 mm, in the range of 2.25 mm to 2.75 mm, and/or in the range of 2.40 mm to 2.50 mm.

The bending radius BR can be about 1.5 mm, about 1.75 mm, about 2.0 mm, about 2.25 mm, about 2.5 mm, about 2.75 mm, about 3.0 mm, about 3.25 mm, and/or about 6.0 mm.

The bending radius BR can be less than about 6.0 mm, less than about 3.25 mm, less than about 3.0 mm, less than about 2.75 mm, less than about 2.5 mm, less than about 2.25 mm, less than about 2 mm, less than about 1.75 mm, and/or less than about 1.5 mm. In an exemplary embodiment, the value of the bending radius BR can be equal to the radius of a receiver head of a bone anchor, e.g., about 2.06 mm, about 2.50 mm, or about 2.81 mm.

In some embodiments, as shown in FIG. 3D, the bent portion 306 can include a transition portion 309. The transition portion 309 can be located at the second end 307b, as shown in FIG. 3D, though it will be appreciated that the transition portion can be located at the first end 307a, or at both ends. The transition portion of the rod is the point at which the bent portion 306 transitions from one diameter to another diameter. The transition portion can include a transition radius TR which, as shown, can be the radius of curvature of the transition portion 309 at a junction between the second rod 304 and the second end 307b of the bent portion 306, though it will be appreciated that the transition radius can be located at a junction between the first rod 302 and the first end 307a of the bent portion 306. In the illustrated embodiment of FIG. 3D, the bending radius BR is equal to the transition radius TR, though it will be appreciated that the bending radius BR can be smaller or larger than the transition radius TR. By matching or substantially matching the bending radius BR to the transition radius TR, a bend in the rod can be formed as close as possible to the transition, advantageously minimizing the length L of the bent portion 306 and allowing the implant to fit within increasingly narrow spaces when implanted. In some embodiments, the rod can be bent using a manufacturing die having a radius that matches the bending radius BR and the transition radius TR, such that the die conforms to and fits snugly within the space between the bend and the transition. It will be appreciated that the values of the transition radius TR can fall within the same ranges discussed with regard to the bending radius BR above, though values of the transition radius can also differ.

The length L of the bent portion 306 can vary based on factors such as the diameter of the rods 302, 304, the desired offset between the rods, and the bending radius BR and the transition radius TR of the bent portion. The length L can be in the range of 5 mm to 20 mm, in the range of 7 mm to 14 mm, in the range 9 mm to 13 mm, in the range of 10 mm to 12 mm, and/or in the range of 11 to 11.5 mm. In an exemplary embodiment, the length L can be about 8.6 mm or about 11.33 mm.

The length L can be about 20 mm, about 15 mm, about 14 mm, about 13 mm, about 12 mm, about 11 mm, about 10 mm, about 9 mm, about 8 mm, about 7 mm, and/or about 5 mm.

The length L can be less than about 20 mm, less than about 15 mm, less than about 14 mm, less than about 13 mm, less than about 12 mm, less than about 11 mm, less than about 10 mm, less than about 9 mm, less than about 8 mm, less than about 7 mm and/or less than about 5 mm.

The ratio between the length L and the bending radius BR can be in the range of 3.0 to 13.30, in the range of 3.25 to 4.50, in the range of 3.45 to 4.25, in the range of 3.75 to 4.0, and/or in the range of 3.8 to 3.9. The ratio between the length L and the bending radius BR can be about 13.30. about 4.50, about 4.25, about 4.0, about 3.9, about 3.8, about 3.75, about 3.45, about 3.25, and/or about 3.0. The ratio between the length L and the bending radius BR can be less than about 13.30, less than about 4.50, less than about 4.25, less than about 4.0, less than about 3.9, less than about 3.8, less than about 3.75, less than about 3.45, less than about 3.25, and/or less than about 3.0.

The offset OC between the rods 302, 304 can vary based on factors such as the diameter of the rods 302, 304, the spacing between bone anchors with which the implant 300 is to be used, the size of bone anchors with which the implant is to be used, anatomical dimensions of the patient, and so forth. The offset OC can be in the range of 3 mm to 15 mm, in the range of 4 mm to 9 mm, in the range of 5 mm to 8 mm, in the range of 6 mm to 7 mm. In an exemplary embodiment, the offset OC can be about 6 mm or 6.75 mm.

The offset OC can be about 15 mm, about 10 mm, about 9 mm, about 8 mm, about 7 mm, about 6 mm, about 5 mm, about 4 mm, and/or about 3 mm.

The offset OC can be less than about 15 mm, less than about 10 mm, less than about 9 mm, less than about 8 mm, less than about 7 mm, less than about 6 mm, less than about 5 mm, less than about 4 mm, and/or less than about 3 mm.

The ratio between the offset OC and the bending radius BR can be in the range of 2.0 to 3.0, in the range of 2.1 to 2.9, in the range of 2.25 to 2.75, and/or in the range of 2.4 to 2.5. The ratio between the offset OC and the bending radius BR can be about 3.0, about 2.9, about 2.75, about 2.5, about 2.4, about 2.25, about 2.1, and/or about 2.0. The ratio between the offset OC and the bending radius BR can be less than about 3.0, less than about 2.9, less than about 2.75, less than about 2.5, less than about 2.4, less than about 2.25, less than about 2.1, and/or less than about 2.0.

The ratio between the length L and the offset OC can be in the range of 1.0 to 2.0, in the range of 1.25 to 1.75, in the range of 1.40 to 1.66, and/or in the range of 1.50 to 1.55. The ratio between the length L and the offset OC can be about 2.0, about 1.75, about 1.67, about 1.55, about 1.50, about 1.40, about 1.25, and/or about 1.0. The ratio between the length L and the offset OC can be less than about 2.0, less than about 1.75, less than about 1.67, less than about 1.55, less than about 1.50, less than about 1.40, less than about 1.25, and/or less than about 1.0.

Figure 4B:
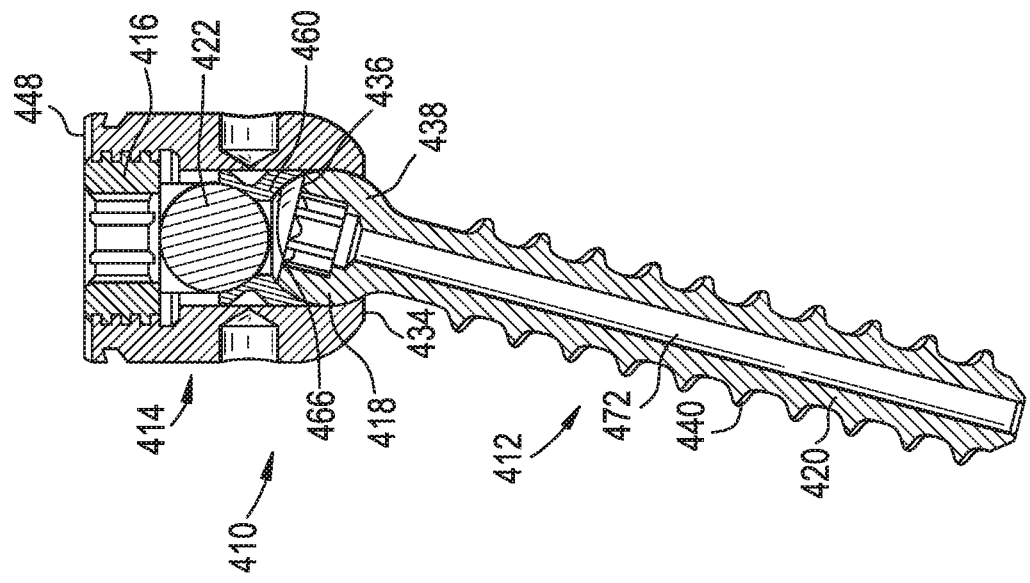
FIG. 4B is a sectional view of the bone anchor assembly of FIG. 4A.
Figure 4A:
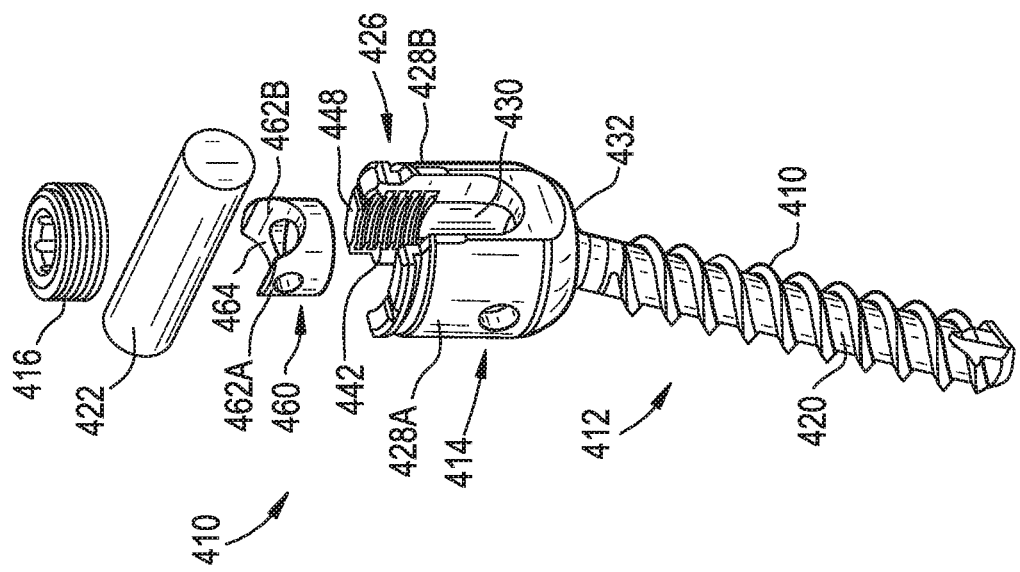
FIG. 4A is an exploded perspective view of a prior art bone anchor assembly.

FIGS. 4A-4B illustrate a prior art bone anchor assembly 410 that can be used with the implants 100, 200, 300 disclosed herein. The bone anchor assembly 410 includes a bone anchor 412, a head or receiver member 414 for receiving a spinal fixation element, such as a spinal rod 422, to be coupled to the bone anchor 412, and a closure mechanism or set screw 416 to capture a spinal fixation element within the receiver member 414 and fix the spinal fixation element with respect to the receiver member 414. The bone anchor 412 includes a proximal head 418 and a distal shaft 420 configured to engage bone. The receiver member 414 has a proximal end 426 having a pair of spaced apart arms 428A, 428B defining a recess 430 therebetween and a distal end 432 having a distal end surface 434 defining an opening through which at least a portion of the bone anchor 412 extends. The closure mechanism 416 can be positionable between and can engage the arms 428A, 428B to capture a spinal fixation element, e.g., a spinal rod 422, within the receiver member 414 and fix the spinal fixation element with respect to the receiver member 414.

The proximal head 418 of the bone anchor 412 is generally in the shape of a truncated sphere having a planar proximal surface 436 and an approximately spherically-shaped distal surface 438. The illustrated bone anchor assembly is a polyaxial bone screw designed for posterior implantation in the pedicle or lateral mass of a vertebra. The proximal head 418 of the bone anchor 412 engages the distal end 432 of the receiver member 414 in a ball and socket like arrangement in which the proximal head 418 and the distal shaft 420 can pivot relative to the receiver member 414. The distal surface 438 of the proximal head 418 of the bone anchor 412 and a mating surface within the distal end 432 of the receiver member 414 can have any shape that facilitates this arrangement, including, for example, spherical (as illustrated), toroidal, conical, frustoconical, and any combinations of these shapes.

The distal shaft 420 of the bone anchor 412 can be configured to engage bone and, in the illustrated embodiment, includes an external bone engaging thread 440. The thread form for the distal shaft 420, including the number of threads, the pitch, the major and minor diameters, and the thread shape, can be selected to facilitate connection with bone. The distal shaft 420 can also include other structures for engaging bone, including a hook. The distal shaft 420 of the bone anchor 412 can be cannulated, having a central passage or cannula 472 extending the length of the bone anchor to facilitate delivery of the bone anchor over a guidewire in, for example, minimally-invasive procedures. Other components of the bone anchor assembly 410, including, for example, the closure mechanism 416, the receiver member 414, and the compression member 460 (discussed below) can be cannulated or otherwise have an opening to permit delivery over a guidewire. The distal shaft 420 can also include one or more sidewall openings or fenestrations that communicate with the cannula to permit bone in-growth or to permit the dispensing of bone cement or other materials through the bone anchor 412. The sidewall openings can extend radially from the cannula through the sidewall of the distal shaft 420. The distal shaft 420 of the bone anchor 412 can also be coated with materials to permit bone growth, such as, for example, hydroxyapatite, and the bone anchor assembly 410 can be coated partially or entirely with anti-infective materials, such as, for example, tryclosan.

The proximal end 426 of the receiver member 414 includes a pair of spaced apart arms 428A, 428B defining a U-shaped recess 430 therebetween for receiving a spinal fixation element, e.g., a spinal rod 422. Each of the arms 428A, 428B can extend from the distal end 432 of the receiver member 414 to a free end. The outer surfaces of each of the arms 428A, 428B can include a feature, such as a recess, dimple, notch, projection, or the like, to facilitate connection of the receiver member 414 to instruments. For example, the outer surface of each arm 428A, 428B can include an arcuate groove at the respective free end of the arms.

The distal end 432 of the receiver member 414 includes a distal end surface 434 which is generally annular in shape defining a circular opening through which at least a portion of the bone anchor 412 extends. For example, the distal shaft 420 of the bone anchor 412 can extend through the opening.

The bone anchor 412 can be selectively fixed relative to the receiver member 414. Prior to fixation, the bone anchor 412 is movable relative to the receiver member 414 within a cone of angulation generally defined by the geometry of the distal end 432 of the receiver member and the proximal head 418 of the bone anchor 412. The bone anchor 410 can be a favored angle screw or a conventional (non-biased) polyaxial screw in which the bone anchor pivots in the same amount in every direction.

The spinal fixation element, e.g., the spinal rod 422, can either directly contact the proximal head 418 of the bone anchor 412 or can contact an intermediate element, e.g., a compression member 460. The compression member 460 can be positioned within the receiver member 414 and interposed between the spinal rod 422 and the proximal head 418 of the bone anchor 412 to compress the distal outer surface 438 of the proximal head 418 into direct, fixed engagement with the distal inner surface of the receiver member 414. The compression member 460 can include a pair of spaced apart arms 462A and 462B defining a U-shaped seat 464 for receiving the spinal rod 422 and a distal surface 466 for engaging the proximal head 418 of the bone anchor 412.

The proximal end 426 of the receiver member 414 can be configured to receive a closure mechanism 416 positionable between and engaging the arms 428A, 428B of the receiver member 414. The closure mechanism 416 can be configured to capture a spinal fixation element, e.g., a spinal rod 422, within the receiver member 414, to fix the spinal rod 422 relative to the receiver member 414, and to fix the bone anchor 412 relative to the receiver member 414. The closure mechanism 416 can be a single set screw having an outer thread for engaging an inner thread 442 provided on the arms 428A, 428B of the receiver member 414. In other embodiments, however, the closure mechanism 416 can include an outer set screw operable to act on the compression member 460 and an inner set screw operable to act on the rod 422.

The bone anchor assembly 410 can be used with a spinal fixation element such as rigid spinal rod 422. Alternatively, the spinal fixation element can be a dynamic stabilization member that allows controlled mobility between the instrumented vertebrae.

The devices disclosed herein can be used in various surgical procedures to stabilize adjacent bodies. In use, a user makes an incision in a patient at the site of the surgical procedure. The bone anchor assembly 410 can be assembled such that the distal shaft 420 extends through the opening in the distal end 432 of the receiver member 414 and the proximal head 418 of the bone anchor 412 is received in the distal end 432 of the receiver member 414. A driver tool can be fitted with the bone anchor 412 to drive the bone anchor 412 into bone. The user can implant a first bone anchor and a second bone anchor at the surgical site in connection with any of the methods described above. For example, a first bone anchor 402 can be implanted in a first vertebra and a second bone anchor 422 can be implanted in a second vertebra. It will be appreciated that the bone anchors can be implanted in other parts of the spine, such as the thoracic spine, lumbar spine, and so forth, or in other parts of the body, such as the femur, tibia, ulna, etc. The compression member 460 can be positioned within the receiver member 414 such that the arms 462A, 462B of the compression member are aligned with the arms 428A, 428B of the receiver member 414 and the lower surface of the compression member 414 is in contact with the proximal head 418 of the bone anchor 412. A fixation element, e.g., the rod 422, can be located in the recess 430 of the receiver member 414. The closure mechanism 416 can be engaged with the inner thread 442 provided on the arms 428A, 428B of the receiver member 414. A torsional force can be applied to the closure mechanism 416 to move it within the recess 430 so as to force the spinal rod 422 into engagement with the compression member 460 and to in turn force the compression member 460 onto the proximal head 418 of the bone anchor 412, thereby fixing the spinal rod 422 relative to the receiver member 414 and locking the angular position of the bone anchor 412 relative to the receiver member 414.

The implants disclosed herein can be constructed from any of a variety of known materials. Exemplary materials include those which are suitable for use in surgical applications, including metals such as titanium, titanium alloy, cobalt chromium, stainless steel, polymers such as PEEK, ceramics, carbon fiber, and so forth. The various components of the implants disclosed herein can be rigid or flexible. One or more components or portions of the implant can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. The devices disclosed herein can be fully or partially implanted, or can be used in an external fixation system. While the devices and methods disclosed herein are generally described in the context of the spine, it will be appreciated that the methods and devices disclosed herein can be used with any human or animal bone or other tissue, in any of a variety of surgeries performed on humans or animals, and/or in fields unrelated to implants or surgery. While implants having two rods are disclosed herein, in some embodiments the implants can include three or more rods connected by a connector.

Although specific embodiments are described above, it should be understood that numerous changes may be made within the spirit and scope of the concepts described. Accordingly, it is intended that this disclosure not be limited to the described embodiments.

The invention claimed is:

1. An implant, comprising:
a first spinal rod having a first diameter;
a second spinal rod having a second diameter;
a connector having a first end and an opposite, second end disposed between the first spinal rod and the second spinal rod, the connector being formed by a bent portion of the first and second spinal rods, the bent portion having a bending radius and a diameter that is smaller than at least one of the first diameter or the second diameter and tapering continuously from the first diameter to the second diameter;
wherein the connector is configured to be disposed in a space between adjacent vertebrae when the first spinal rod and the second spinal rod are coupled to the adjacent vertebrae.

2. The implant of claim 1, wherein the first spinal rod extends in an opposite direction from the second spinal rod.

3. The implant of claim 1, wherein the first spinal rod extends from the first end of the connector and the second spinal rod extends from the second end of the connector.

4. The implant of claim 1, wherein the first rod and the second rod are formed as a single monolithic unit with the connector.

5. The implant of claim 1, wherein the bent portion is integral with the first and second spinal rods.

6. The implant of claim 5, wherein a length of the bent portion is in a range of 5 mm to 20 mm.

7. The implant of claim 6, wherein a ratio of the length of the bent portion and an offset between the first and second spinal rods is in a range of 1.0 to 2.0 the offset being measured between a central axis A1 of the first spinal rod where the first spinal rod meets the connector and the central axis A2 of the second spinal rod where the second spinal rod meets the connector.

8. The implant of claim 5, wherein the implant further includes a transition portion at a junction between the bent portion and one or more of the first rod and the second rod.

9. The implant of claim 1, wherein the first diameter, the second diameter and the diameter of the bent portion are substantially equal.

10. The implant of claim 1, wherein the bending radius of the bent portion ranges from 1.5 mm to 6 mm.

11. The implant of claim 10, wherein the bending radius of the bent portion is substantially equal to a transition radius of the transition portion.

12. The implant of claim 10, wherein a ratio of an offset between the first and second spinal rods and the bending radius is in a range of 2.0 to 3.0, the offset being measured between a central axis A1 of the first spinal rod where the first spinal rod meets the connector and the central axis A2 of the second spinal rod where the second spinal rod meets the connector.

13. The implant of claim 10, wherein a ratio of the length of the bent portion and the bending radius is in a range of 3.0 to 13.30.

14. The implant of claim 1, wherein the bending radius is substantially equal to a radius of a receiver head of a bone anchor through which the implant is received.

15. The implant of claim 14, wherein a superior surface of the bent portion provides a relief for a portion of the first bone anchor and an inferior surface of the bent portion provides a relief for a portion of the second bone anchor.

16. The implant of claim 1, wherein the connector maintains an offset between the first spinal rod and the second spinal rod, the offset being in a range of 3 mm to 15 mm.

17. A surgical method, comprising:
implanting a first bone anchor in a first vertebra of a spine of a patient;
implanting a second bone anchor in a second, adjacent vertebra of the spine;
positioning an implant comprising a first rod, a second rod, and a bent portion extending between the first and second rods in the first bone anchor and the second bone anchor such that:
the first rod having a first diameter is seated in the first bone anchor;
the second rod having a second diameter is seated in the second bone anchor;
the bent portion is disposed external to the first bone anchor and the second bone anchor to connect the first rod and the second rod such that the first rod is offset from the second rod, the bent portion having a diameter that is smaller than at least one of the first diameter or the second diameter and tapering continuously from the first diameter to the second diameter.

18. The method of claim 17, wherein the offset of the first rod and the second rod is in a range of 3 mm to 15 mm.

19. The method of claim 17, wherein the bent portion has a bending radius that is substantially equal to a radius of a receiver head of one or more of the first bone anchor and the second bone anchor.

20. The method of claim 19, wherein a ratio of the offset and the bending radius is in a range of 2.0 to 3.0.

21. An implant, comprising:
a first rod;
a second rod;
a bent portion connecting the first and second rods such that the first and second rods extend in opposite directions from the bent portion, the bent portion having at least one transition portion at a junction of the bent portion and any of the first and second rods, the at least one transition portion having a varying diameter along its length that tapers into the bent portion,
wherein a bending radius of the bent portion is substantially equal to a transition radius of the transition portion.

22. The implant of claim 21, wherein a bending radius of the bent portion is smaller than a transition radius of the transition portion.

23. The implant of claim 21, wherein the transition radius is in a range of 1.5 mm to 6.0 mm.

* * * * *